United States Patent
Williams et al.

(10) Patent No.: US 10,478,172 B1
(45) Date of Patent: Nov. 19, 2019

(54) METHODS OF TISSUE REPAIR

(71) Applicant: WEST GEN TECHNOLOGIES, L.L.C., Plainview, TX (US)

(72) Inventors: Donald A. Williams, Plainview, TX (US); George J. Sikora, Bridgewater, MA (US)

(73) Assignee: West Gen Technologies, L.L.C., Plainview, TX (US)

( * ) Notice: Subject to any disclaimer, the term of this patent is extended or adjusted under 35 U.S.C. 154(b) by 0 days.

(21) Appl. No.: 16/430,182

(22) Filed: Jun. 3, 2019

Related U.S. Application Data

(60) Provisional application No. 62/680,227, filed on Jun. 4, 2018.

(51) Int. Cl.
| | |
|---|---|
| *A61B 17/58* | (2006.01) |
| *A61B 17/60* | (2006.01) |
| *A61F 2/00* | (2006.01) |
| *A61B 17/04* | (2006.01) |
| *A61B 17/17* | (2006.01) |
| *A61F 2/08* | (2006.01) |
| *A61B 17/00* | (2006.01) |

(52) U.S. Cl.
CPC ...... *A61B 17/0401* (2013.01); *A61B 17/1714* (2013.01); *A61B 17/1796* (2013.01); *A61F 2/0811* (2013.01); *A61B 2017/00986* (2013.01); *A61B 2017/00991* (2013.01); *A61B 2017/0409* (2013.01); *A61F 2002/0852* (2013.01); *A61F 2002/0888* (2013.01)

(58) Field of Classification Search
CPC combination set(s) only.
See application file for complete search history.

(56) References Cited

U.S. PATENT DOCUMENTS

| | | |
|---|---|---|
| 5,147,367 A | 9/1992 | Ellis |
| 5,380,334 A | 1/1995 | Torrie et al. |
| 5,387,213 A | 2/1995 | Breard et al. |
| 5,522,843 A | 6/1996 | Zang |
| 5,725,581 A | 3/1998 | Branemark |
| 5,904,704 A | 5/1999 | Goble et al. |
| 6,139,565 A | 10/2000 | Stone et al. |
| 6,267,766 B1 | 7/2001 | Burkhart |
| 6,635,073 B2 | 10/2003 | Bonutti |
| 7,699,881 B2 | 4/2010 | Willmann |
| 2002/0161401 A1 | 10/2002 | Steiner |
| 2003/0088251 A1 | 5/2003 | Braun et al. |

(Continued)

*Primary Examiner* — Sameh R Boles
(74) *Attorney, Agent, or Firm* — Dickinson Wright PLLC; Mark E. Scott; K. Lance Anderson

(57) ABSTRACT

Methods of tissue repair. At least one example method includes: pulling a tissue in place over a bone location; abutting a distal end of a guide tool against the tissue at a first location, and driving a first bone anchor through a delivery tube of the guide tool, through the tissue, and into the bone at the first location, the first bone anchor coupled to a first suture line; abutting the distal end of the guide tool against the tissue at a second location displaced from the first location, and then driving a second bone anchor through the delivery tube, through the tissue, and into the bone at the second location, the second bone anchor associated with the first suture line; withdrawing the guide tool away from the tissue; and tightening the first suture line to create a first suture over the tissue.

17 Claims, 26 Drawing Sheets

(56) References Cited

U.S. PATENT DOCUMENTS

| | | |
|---|---|---|
| 2003/0204193 A1 | 10/2003 | Gabriel et al. |
| 2004/0153074 A1 | 8/2004 | Bojarski et al. |
| 2004/0267278 A1 | 12/2004 | Overaker |
| 2005/0107828 A1 | 5/2005 | Reese |
| 2005/0267478 A1 | 12/2005 | Corradi et al. |
| 2006/0142784 A1 | 6/2006 | Kontos |
| 2007/0100350 A1 | 5/2007 | Deffenbaugh et al. |
| 2007/0198017 A1 | 8/2007 | Tschakaloff et al. |
| 2008/0009904 A1 | 1/2008 | Bourque et al. |
| 2008/0065120 A1 | 3/2008 | Zannis et al. |
| 2008/0109038 A1 | 5/2008 | Steiner et al. |
| 2008/0167660 A1 | 7/2008 | Moreau et al. |
| 2009/0125071 A1 | 5/2009 | Skinlo et al. |
| 2010/0004683 A1 | 1/2010 | Hoof et al. |
| 2010/0063541 A1 | 3/2010 | Brunelle et al. |
| 2011/0295279 A1 | 12/2011 | Stone et al. |
| 2012/0109156 A1* | 5/2012 | Overes ............... A61B 17/0057 606/139 |
| 2013/0079813 A1 | 3/2013 | Li et al. |
| 2013/0190570 A1 | 7/2013 | Hirsch et al. |
| 2014/0081281 A1 | 3/2014 | Felder |
| 2014/0364862 A1 | 12/2014 | Bennett et al. |
| 2016/0278760 A1 | 9/2016 | McDevitt |

* cited by examiner

METHODS OF TISSUE REPAIR

CROSS-REFERENCE TO RELATED APPLICATIONS

This application claims the benefit of U.S. Provisional Application No. 62/680,227 titled "Bone Anchor and Suture System, Tool for Implanting Same, and Method of Implanting Same." The provisional application is incorporated by reference herein as if reproduced in full below.

BACKGROUND

There are many examples in the medical field of using fixation devices, such as bone anchors, and sutures to facilitate tissue repair. For example, a rotator cuff tear is an injury in which tendons or muscles in the shoulder may tear or separate from the upper head of the humerus. Repair of such a rotator cuff injury may include reattaching the torn or separated tissue to the underlying bone at an appropriate location on the greater tuberosity of the upper head of the humerus. In many cases, the reattachment of the tissue may take place arthroscopically. While arthroscopic surgeries are less invasive than open surgical procedures, all surgical procedures carry risks and some of the risks increase with increasing time to perform the surgical procedure. Thus, any method, system, and/or procedure which reduces an amount of time to surgically complete a tissue repair would provide a competitive advantage in the marketplace.

SUMMARY

One example is a method of connecting tissue to a bone, comprising: pulling a tissue in place over a bone location; abutting a distal end of a guide tool against the tissue at a first location, and driving a first bone anchor through a delivery tube of the guide tool, through the tissue, and into the bone at the first location, the first bone anchor coupled to a first suture line; abutting the distal end of the guide tool against the tissue at a second location displaced from the first location, and then driving a second bone anchor through the delivery tube, through the tissue, and into the bone at the second location, the second bone anchor associated with the first suture line; withdrawing the guide tool away from the tissue; and tightening the first suture line to create a first suture over the tissue.

In the example method driving the first bone anchor may further comprise: telescoping a first tack wire through a guide tube of the guide tool; drilling a distal end of the first tack wire through the tissue and into the bone; bending a proximal end of the first tack wire into a slot within a handle of the guide tool; telescoping a first drill wire though the delivery tube of the guide tool, the delivery tube parallel to the guide tube; drilling with the first drill wire through the tissue and into the bone to create a first pilot hole in the bone; removing the first drill wire from the guide tool; and telescoping the first bone anchor through the delivery tube into the first pilot hole. Telescoping the first drill wire may further comprise telescoping the first drill wire through a drill guide cartridge mated with a handle of the guide tool, the drill guide cartridge defines a passageway with a longitudinal central axis that is coaxial with a longitudinal central axis of the delivery tube. Drilling with the first drill wire may further comprise drilling with the first drill wire telescoped through the drill guide cartridge. Telescoping the first bone anchor through the delivery tube may further comprise: mating an anchor cartridge with a handle of the guide tool, the anchor cartridge having a first delivery lumen with the first bone anchor disposed therein, and a second delivery lumen with the second bone anchor disposed therein, and after mating the first delivery lumen is coaxial with the first delivery lumen; pushing the first bone anchor out the first delivery lumen, through the delivery tube, and into the first pilot hole by way of a delivery camp. Driving the second bone anchor may further comprise: removing the anchor cartridge from the handle of the guide tool; mating the anchor cartridge with the handle of the guide tool such that the second delivery lumen is coaxial with the delivery tube; and pushing the second bone anchor out of the second delivery lumen, through the delivery tube, and into a second pilot hole. The example method may further comprise: abutting the distal end of the guide tool against the tissue at a third location; telescoping a third drill wire though the second delivery lumen; drilling with the third drill wire through the tissue and into the bone to create a third pilot hole in the bone; removing the third drill wire from the second delivery lumen; removing the anchor cartridge from the handle of the guide tool; mating the anchor cartridge with the handle of the guide tool such that a third delivery lumen is coaxial with the delivery tube; and pushing a third bone anchor out of the third delivery lumen, through the delivery tube, and into a third pilot hole. The example method may further comprise: abutting the distal end of the guide tool against the tissue at a fourth location; telescoping a fourth drill wire though the third delivery lumen; drilling with the fourth drill wire through the tissue and into the bone to create a fourth pilot hole in the bone; removing the fourth drill wire from the third delivery lumen; removing the anchor cartridge from the handle of the guide tool; mating the anchor cartridge with the handle of the guide tool such that a fourth delivery lumen is coaxial with the delivery tube; and pushing a fourth bone anchor out of the fourth delivery lumen, through the delivery tube, and into a third pilot hole.

In the example method, after telescoping the first bone anchor into the first pilot hole, the example method may further comprise extracting the first suture line from the guide tool through a slot in the delivery tube. In the example method driving the second bone anchor may further comprise: abutting the distal end of the guide tool against the tissue at the second location displaced from the first location; telescoping a second tack wire through the guide tube of the guide tool; drilling a distal end of the second tack wire through the tissue and into the bone; bending a proximal end of second tack wire into the slot within the handle of the guide tool; telescoping a second drill wire though the delivery tube of the guide tool; drilling with the second drill wire through the tissue and into the bone to create a second pilot hole in the bone; removing the second drill wire; telescoping the second bone anchor through the delivery tube into the second pilot hole; and removing the guide tool including the second tack wire.

Telescoping the first drill wire in the example method may further comprise telescoping the first drill wire through a drill guide cartridge mated with a handle of the guide tool, the drill guide cartridge defines a passageway with a longitudinal central axis that is coaxial with a longitudinal central axis of the delivery tube, Drilling with the first drill wire in the example method may further comprise drilling with the first drill wire telescoped through the drill guide cartridge.

In the example method telescoping the first bone anchor through the delivery tube may further comprise: mating an anchor cartridge with a handle of the guide tool, the anchor cartridge having a first delivery lumen with the first bone anchor disposed therein, and a second delivery lumen with the second bone anchor disposed therein, and after mating the delivery tube is coaxial with the first delivery lumen; and pushing the first bone anchor out the first delivery lumen, through the delivery tube, and into the first pilot hole by way of a delivery camp.

In the example method telescoping the second drill wire may further comprise telescoping the second drill wire through the first delivery lumen of the anchor cartridge. And drilling with the second drill wire may further comprise drilling with the second drill wire telescoped through first delivery lumen of the anchor cartridge. Telescoping the second bone anchor through the delivery tube into the second pilot hole may further comprise: removing the anchor cartridge from the handle of the guide tool; mating the anchor cartridge with the handle of the guide tool such that the second delivery lumen is coaxial with the delivery tube; and pushing the second bone anchor out of the second delivery lumen, through the delivery tube, and into a second pilot hole. In some cases, the first drill wire and the second drill wires are the same wires.

In the example method tightening the first suture line to create the first suture may further comprise tightening a second suture line coupled the second bone anchor, the second suture line having a loop that extends through a loop of the first suture line.

In the example method tightening the first suture line to create the first suture may further comprise pulling a tightening end of the first suture line to make a loop defined by the first suture line smaller, the loop of the first suture line extends through an eyelet of an eye splice coupled to the second bone anchor.

The example method may further comprise: abutting the distal end of the guide tool against the tissue at a third location, and driving a third bone anchor through a delivery tube of the guide tool, through the tissue, and into the bone at the third location, the third bone anchor coupled to a second suture line; abutting the distal end of the guide tool against the tissue at a fourth location displaced from the first location, and then driving a fourth bone anchor through the delivery tube, through the tissue, and into the bone at the fourth location, the second bone anchor associated with the second suture line; and tightening the second suture line to create a second suture over the tissue.

BRIEF DESCRIPTION OF THE DRAWINGS

For a detailed description of example embodiments, reference will now be made to the accompanying drawings (not necessarily to scale) in which.

Throughout the drawing figures, like reference numbers should be understood to refer to like elements, features, and structures.

Definitions

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

"About" in relation to a dimension will be the recited dimension plus or minus ten percent (10%).

"Central axis" shall mean a longitudinal axis of a structure or portion thereof, but shall not be read to be an axis of symmetry unless expressly stated.

"Counter bore" shall refer to a shape without regard a method of creation. Thus, a counter bore may be created by a boring, but may also be created by casting the counter bore, milling to create the counter bore, and drilling to create the counter bore.

Relative locations may be described as "distal" and "proximal", and in such cases a device or portion described as "distal" to a location will be closer to the distal end of the guide tool relative to the location, and a device or portion described as "proximal" to a location will be closer to the proximal end of the guide tool relative to the location.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various example embodiments may be directed to: guide tools for tissue repairs that may involve suturing tissue to an underlying bone location; bone anchor cartridges carrying preloaded and pre-tied fixation devices or bone anchors along with suture lines; and related methods of using the guide tools and bone anchor cartridges. The specification below presents the guide tool, and then various cartridges that may be used in conjunction with the guide tool. Once the example guide tool and cartridges are introduced, the specification turns to example methods of using the guide tool and cartridges to facilitate tissue repair that is faster and easier than related art tissue repair.

The Guide Tool

Figure 1:
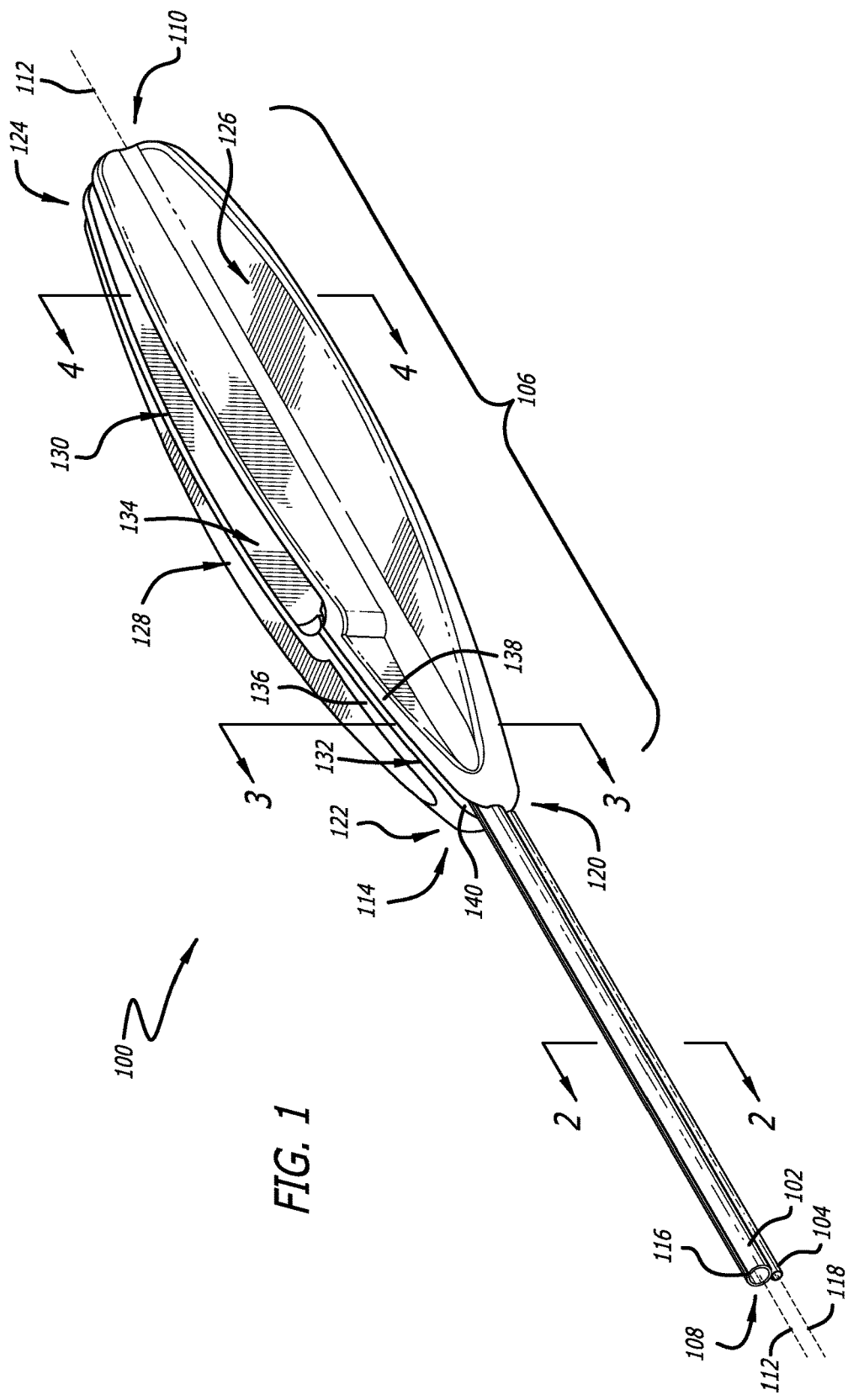
FIG. 1 shows a perspective view of a guide tool in accordance with at least some embodiments.

FIG. 1 shows a perspective view of a guide tool in accordance with at least some embodiments. In particular, FIG. 1 shows a guide tool 100 comprising a delivery tube 102, a guide tube 104, and a handle 106. Inasmuch as the guide tool 100 may be held by the handle 106 and used to install bone anchors through the delivery tube 102, the example guide tool 100 defines a distal end 108 and a proximal end 110. The example delivery tube 102 defines a longitudinal central axis 112, a distal end that defines the distal end 108 of the guide tool 100, and a proximal end 114. In example cases, the proximal end 114 of the delivery tube 102 is embedded within the handle 106. The example delivery tube 102 defines a slot 116 that runs parallel to the longitudinal central axis 112 from the distal end 108 to the proximal end 114 of the delivery tube 102 (though the portion of slot 116 within the handle 106 is not visible in FIG. 1).

The example guide tool 100 further comprises the guide tube 104 coupled to the delivery tube 102. The guide tube 104 defines a longitudinal central axis 118, a distal end that again defines the distal end 108 of the guide tool 100, and a proximal end 120. In example cases, the proximal end 120 of the guide tube 104 is embedded within the handle 106. The longitudinal central axis 118 of the guide tube 104 is parallel to and offset from the longitudinal central axis 112 of the delivery tube 102. The example guide tube 104 directly abuts the delivery tube 102, but in other case the guide tube 104 may be offset or separated from the delivery tube 102 (e.g. 0.1 to 1 millimeters (mm), inclusive). The guide tube 104 may be coupled to the delivery tube 102 in any suitable fashion, such as by way of a solder connection, laser welding, or an adhesive (e.g., epoxy).

Figure 2:
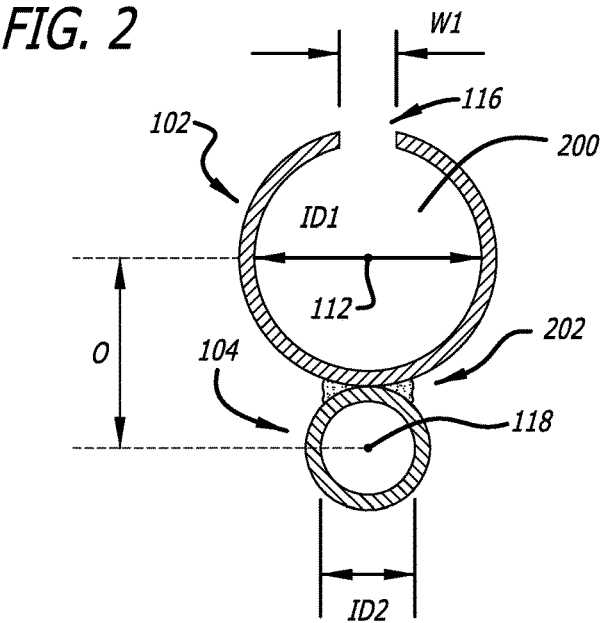
FIG. 2 shows a cross-sectional view of a delivery tube and a guide tube taken substantially along line 2-2 of the FIG. 1, and in accordance with at least some embodiments.

FIG. 2 shows a cross-sectional view of the delivery tube 102 and the guide tube 104 taken substantially along line 2-2 of the FIG. 1, and in accordance with at least some embodiments. In particular, in the view of FIG. 2 the longitudinal central axis 112 of the delivery tube 102 is perpendicular to the plane of the page, and thus is shown as a point. In example embodiments, the delivery tube 102 is made of metallic material (e.g., hypodermic stainless steel). However, any suitable material may be used, particularly taking into account that the guide tool 100 is in most cases a single use disposable item. Also visible in the view of FIG. 2 is the slot 116. The slot 116 may be created in any suitable fashion, such as by cutting (e.g., laser cutting) the wall of the guide tube 104 to remove metallic material and thus create the slot 116. In other cases, the guide tube 104 may be originally created (e.g., extruded) with the slot 116 already in place.

The example delivery tube 102 has internal diameter ID1 that may take any suitable size. The internal diameter ID1 of the delivery tube 102 is selected, designed, and/or constructed to accommodate an expected bone anchor size. For example, if the guide tool 100 (FIG. 1) is to be used with a bone anchor that has an effective diameter of about 2.4 mm, then the inside diameter ID1 of the delivery tube 102 may be larger than the largest expected effective diameter of the bone anchor by between 0.1 mm to 1.5 mm, inclusive. Thus, for a guide tool 100 for use with bone anchors having an effective diameter of 2.5 mm, the inside diameter ID1 may range from 2.6 mm to 3.0 mm, inclusive. The slot 116 has a width W that is equal to or less than half the inside diameter ID1 of the delivery tube 102. As will become more clear below, the slot 116 is used to remove or extract suture lines from the guide tool 100 when moving between bone anchor locations, and/or after the final bone anchor has been installed. Thus, the width W of the slot is large enough to enable the suture lines to be removed from the internal volume 200 of the delivery tube 102. In example cases, the width W1 of the slot may be between 0.2 mm to 1.5, inclusive.

FIG. 2 further shows the guide tube 104. In the view of FIG. 2, the longitudinal central axis 118 of the guide tube 104 is perpendicular to the plane of the page, and thus is shown as a point. In example embodiments, the guide tube 104 is made of metallic material (e.g., hypodermic stainless steel). However, any suitable material may be used, particularly taking into account that the example guide tool 100 is in most cases a single use disposable item. Moreover, the material from which the guide tube 104 is constructed need not be the same as the material from which the delivery tube 102 is constructed.

The example guide tube 104 has internal diameter ID2 that may be any suitable size. In example cases, the internal diameter ID2 of the guide tube 104 is selected, designed, and/or constructed to accommodate an expected size of tack wires (discussed more below) used to hold the guide tool 100 (FIG. 1) in place during the surgical procedures. For example, the inside diameter ID2 of the guide tube 104 may be larger than the largest expected diameter of the tack wire by between 0.05 mm to 1.0 mm, inclusive. It follows that if the tack wire to be used with the guide tool 100 (FIG. 1) has a diameter of about 1.1 mm, the inside diameter ID2 of the guide tube 104 may range from 1.15 mm to 2.1 mm, inclusive.

The guide tube 104 is coupled to the delivery tube 102. In example cases the guide tube 104 abuts the delivery tube 102, and is held in place by any suitable material, such as solder, adhesive (e.g., epoxy), or even metallic material of the tubes themselves (e.g., created from laser welding). The offset O between the longitudinal central axis 118 of the guide tube 104 and the longitudinal central axis 112 of the delivery tube 102 is dependent upon the respective inside diameters ID1 and ID2, the wall thickness of the tubes, and any separation between outside surfaces of the tubes. In the example case of the guide tube 104 abutting the delivery tube 102, the offset O will be the sum of the radius of the outside diameter of the guide tube 104 and the radius of the outside diameter of the delivery tube 102.

The example delivery tube 102 and guide tube 104 are shown to be separate and distinct tubes coupled together in a suitable fashion during the manufacturing process. However, the set of tubes may be created in any suitable fashion. For example, the two tubes may be simultaneously created in an extrusion process (with or without the slot 116), and in such cases the material used to couple the individual tubes is not needed. As another example, the two tubes may be created from a single tube of larger inside diameter that is crimped to form the two tubes. Moreover, the crimping need not fluidly isolate the two tubes; a channel or slot may exist between the two tubes without negating their status as tubes and without adversely affecting use or operation of the guide tool 100 (FIG. 1).

Returning to FIG. 1, the example handle 106 itself defines a distal end 122 and a proximal end 124. The distal end 122 of the handle 106 couples to the proximal end 114 of the delivery tube 102 (and the proximal end of the guide tube 104). In some cases, the proximal ends of the delivery tube 102 and the guide tube 104 are cast in place within the handle 106 during creation of the handle 106. In other cases, the delivery tube 102 and the guide tube 104 are inserted into the handle 106 after creation of the handle 106, such as by vibration welding. The delivery tube 102 and the guide tube 104 may extend into the handle 106 any suitable distance to meet or exceed a predetermined pullout force (e.g., about 70 Newtons of force). In some example cases, the delivery tube 102 and guide tube 104 may extend into the handle 106 by between 5 mm and 20 mm, inclusive, and in a particular case between 10 mm and 15 mm, inclusive.

The example handle 106 defines a longitudinal central axis that is coaxial with the longitudinal central axis 112 of the delivery tube 102 (and thus the longitudinal central axis of the handle 106 is not specifically re-numbered). It follows that the longitudinal central axis of the handle 106 is parallel to and offset from the longitudinal central axis 118 of the guide tube 104. However, in other cases the longitudinal central axis of the handle 106 may be coaxial with the longitudinal central axis 118 of the guide tube 104.

The example handle 106 defines a plurality of vanes, three of which are visible in the perspective view of FIG. 1. In particular, the example handle 106 defines vanes 126, 128, and 130. The example handle 106 further defines a fourth vane that is not visible in FIG. 1, but that will be discussed more below. The vane 126 projects outward along a first radial direction (with radial directions centered at the longitudinal central axis of the handle 106). The vane 128 extends outward along a second radial direction opposite that of the vane 126, and thus the vanes 126 and 128 define and reside in the same plane. The vane 130 is disposed between vane 126 and 128. The example vane 130 extends outward along a radial direction perpendicular from the plane defined by the vane 126 and the vane 128. Other relationships of the vanes are possible in alternative embodiments.

The vane 130 may be conceptually, though not necessarily physically, divided into a channel region 132 and a receptacle 134. In particular, the channel region 132 includes a wall 136 on a first side of the slot 116, and includes another wall 138 on a second side of the slot 116. The wall 136 and the wall 138 together define a channel 140 into an interior of the delivery tube 102 through the slot 116.

Figure 3:
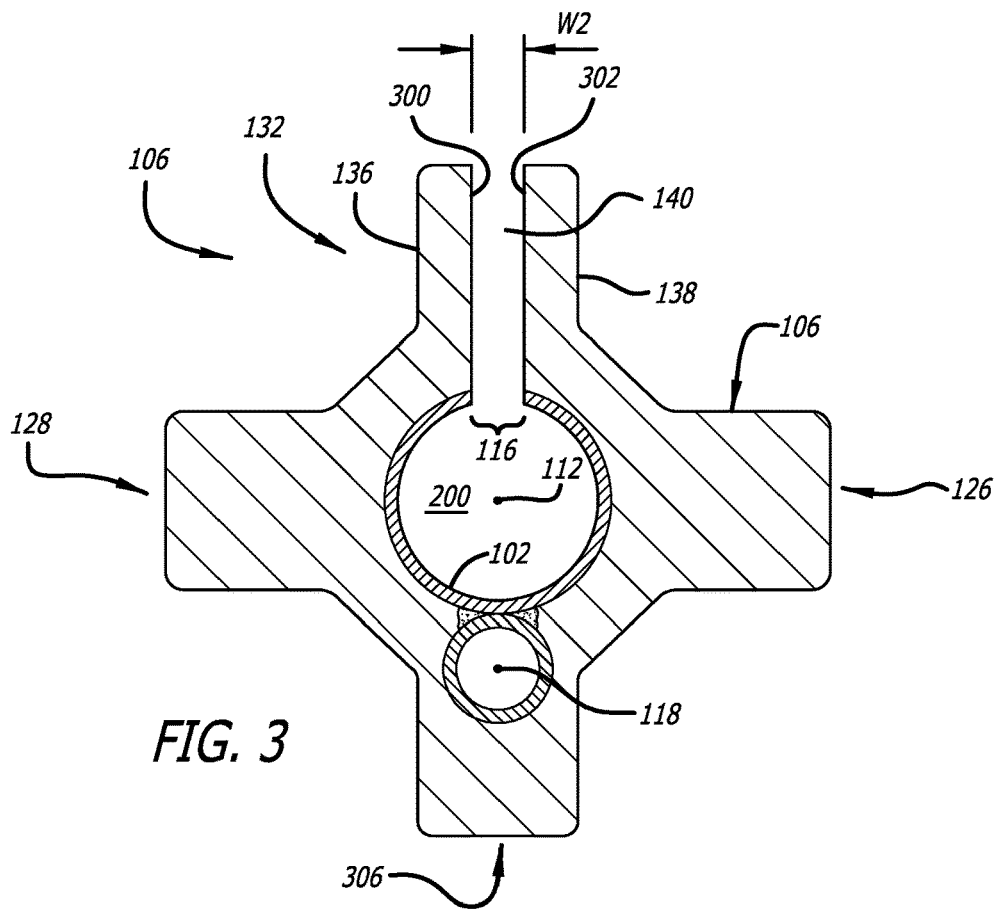
FIG. 3 shows a cross-sectional view of the handle taken substantially along lines 3-3 of FIG. 1, and in accordance with at least some embodiments.

FIG. 3 shows a cross-sectional view of the handle 106 taken substantially along lines 3-3 of FIG. 1, and in accordance with at least some embodiments. In particular, shown in FIG. 3 is a portion of the delivery tube 102 and the guide tube 104 disposed within the handle 106. The example channel region 132 includes the wall 136 defining a surface 300 aligned with a first side of the slot 116. The wall 138 defines a surface 302 facing the wall 136 and aligned with a second side of the slot 116. The surface 300 defines and resides in a plane. The surface 302 defines and resides in a plane. And in the example of FIG. 3, the planes defined by the surfaces 300 and 302 are parallel to each other. Stated otherwise, the surfaces 300 and 302 are parallel to each other. In other cases, however, the surfaces 300 and 302 need not be parallel to each other (e.g., the surfaces 300 and 302 may defines planes that diverge with increasing distance from the longitudinal central axis of the delivery tube 102 and handle 106). The surfaces 300 and 302 thus define the channel 140 into the internal volume 200 of the delivery tube 102 through the slot 116. The example channel 140 has a width W2. In some embodiments, the width W2 is about the same as the width W1 (FIG. 2) of the slot 116 (e.g., the same within manufacturing tolerances). However, the width W2 need not be the same, and can be larger or smaller than the width W1. As discussed more below, the slot 116 and channel 140 provide a path to remove or retract suture lines from the guide tool 100 (FIG. 1) during repositioning of the guide tool 100 or removal of the guide tool 100 from the surgical site after the last bone anchor has been inserted. Thus, the width W2 is wide enough to enable removal or retraction of the suture lines, without regard to the width W1 of the slot 116.

FIG. 3 also shows a cross-sectional view of the vane 126 and the vane 128. The example vanes 126 and 128 extend outward along two distinct radial directions from the longitudinal central axis (not specifically shown) of the handle 106. Also visible in the view of FIG. 3 is a fourth vane 306. In the location of the cross-sectional view of FIG. 3, the fourth vane 306 is solid and extends outward along a radial direction opposite the radial direction of the vane 130. Proximally from the location of the view of FIG. 3, the vane 130 has additional features that will be discussed more below.

Returning to FIG. 1, the example vane 130 defines not only the channel region 132, but also defines a receptacle 134. The receptacle 134 is the location into which various devices are inserted to assist with performing surgical procedures, such as a drill guide cartridge and a bone anchor cartridge. The discussion now turns to example receptacle.

Figure 4:
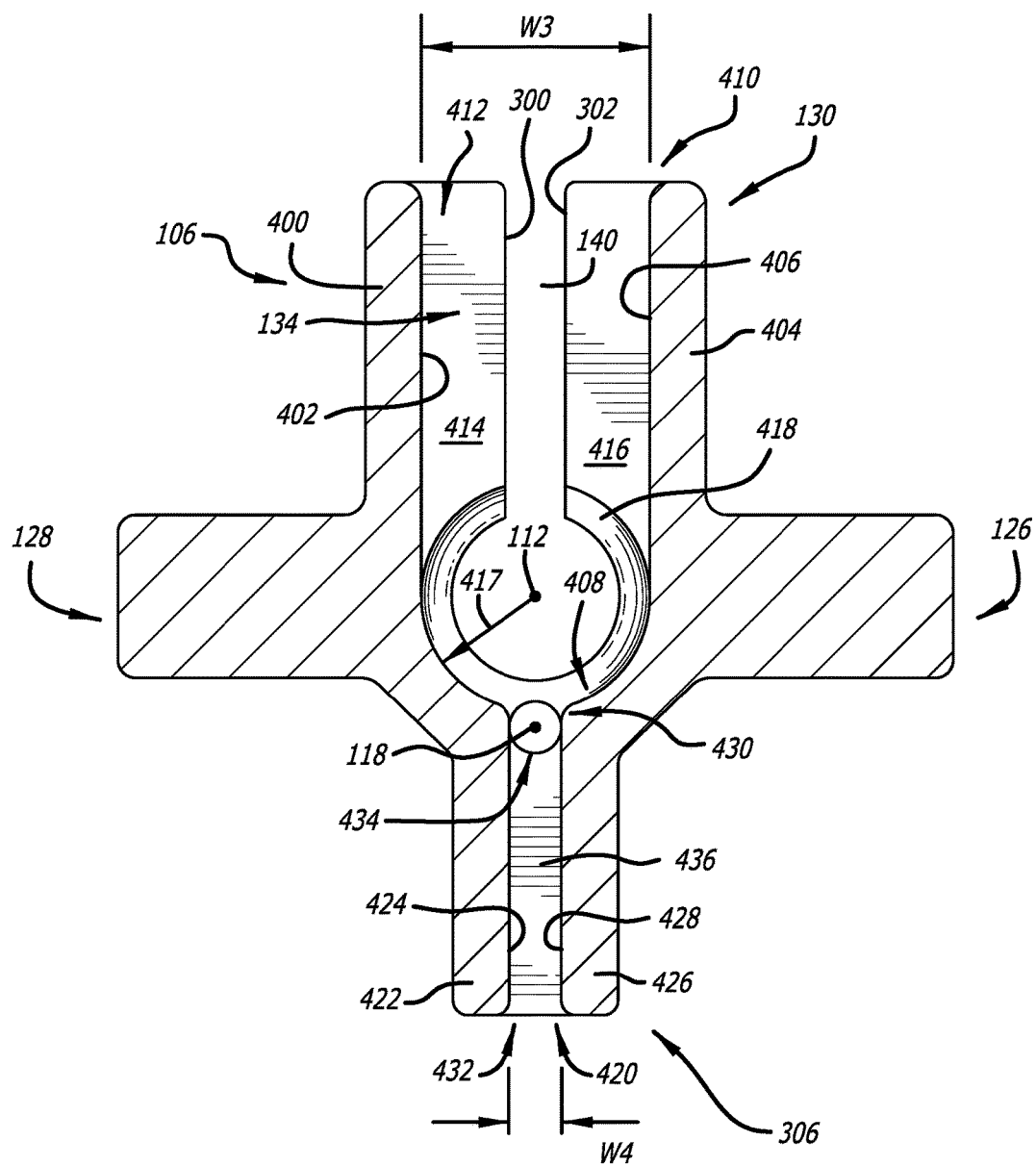
FIG. 4 shows a cross-sectional view of the handle taken substantially along line 4-4 of FIG. 1, and in accordance with at least some embodiments.

FIG. 4 shows a cross-sectional view of the handle 106 taken substantially along line 4-4 of FIG. 1 (e.g., through the receptacle 134), and in accordance with at least some embodiments. In particular, visible in FIG. 4 are the vanes 126, 128, 130, and 306. Other than being longer (measured from the longitudinal central axis 112) because the cross-sectional view of FIG. 4 is taken in a "thicker" part of the handle 106, the vanes 126 and 128 are unchanged. The vane 306 has additional features that are discussed in more detail below. Referring then to the vane 130 in the region of the receptacle 134, the vane 130 defines a wall 400 that has a surface 402. An outer (relative to the longitudinal central axis 112) portion of the surface 402 defines a plane that is perpendicular to the plane of the page. The plane defined by surface 402 is parallel to the plane defined by surface 300. The vane 130 further defines a wall 404 that has a surface 406. An outer (relative to the longitudinal central axis 112) portion of the surface 406 defines a plane that is perpendicular to the plane of the page. The plane defined by surface 406 that is parallel to the plane defined by surface 302. Moreover, the plane defined by surface 406 is parallel to the plane defined by surface 402. The surface 402 and the surface 406 face each other, and the surfaces 402 and 406 define an open top 410 and couple to and/or define a bottom 408. The walls 400 and 404 thus define a channel 412 with the bottom 408 and open top 410. The example channel 412 has a width W3 that is greater than the width of W2 (FIG. 3) of the channel 140. Nevertheless, the channel 412 defined by the walls 400 and 404 is aligned with the channel 140 that is more distal on the handle 106. The wider width W3 of channel 412 thus creates a shoulder 414 between wall 400 and wall 136 (FIG. 3). Similarly, the wider width W3 of channel 412 creates a shoulder 416 between wall 404 and wall 138 (FIG. 3). The shoulders 414 and 416 may be considered to conceptually divide the receptacle 134 and the channel region 132 (FIG. 1).

In the example case of FIG. 4, the bottom 408 defines a radius of curvature 417 having a center that is aligned with resides on the longitudinal central axis 112 of the delivery tube 102 (not visible in FIG. 4). It follows that the longitudinal central axis 112 of the delivery tube 102 extends along the channel 412 between the bottom 408 and the open top 410, and thus the bottom at least partially circumscribes the longitudinal central axis 112. In example embodiments the radius of curvature 417 is greater than half the inside diameter ID1 (FIG. 2) of the delivery tube 102 (FIG. 1). The example radius of curvature 417, being greater than half the inside diameter of delivery tube 102 creates a transition region or counter bore 418 that transitions between two regions of different sizes. As discussed more below, the counter bore 418 defines a region into which a distal tip or projection of the bone anchor cartridge protrudes to help hold the bone anchor cartridge within the receptacle 134 during use. While the bottom 408 of the example channel 412 has a radius of curvature 417, the bottom 408 need not be circular in other embodiments. For example, the bottom 408 could be defined by bottom walls that are perpendicular to the outer portions of surfaces 402 and 406, or the bottom 408 could have multiple flat surfaces that together form the bottom 408. The bottom 408 provides a location against which the bone anchor cartridge may abut, and the bottom 408 need not be a negative image of an abutting surface of the bone anchor cartridge (or vice versa).

Still referring to FIG. 4, and switching to the bottom portion of the figure, in example embodiments the vane 306 of the handle 106 defines a slot 420. In particular, the example vane 306 includes wall 422 defining a surface 424. In example cases, the surface 424 defines a plane that is perpendicular to the plane of the page. The example vane 306 further includes wall 426 defining a surface 428 facing the surface 424. Surface 428 defines a plane that is perpendicular to the plane of the page, and in some cases the surface 428 is parallel to surface 424. The surfaces 424 and 428 define an open top 432 and the surfaces 424 and 428 coupled to and/or define an open bottom 430 that opens into and is in fluid communication with the receptacle 134. The open bottom 430 resides between the longitudinal central axis 118 of the guide tube 104 and the longitudinal central axis 112 of the delivery tube 102. It follows that the longitudinal central axis 118 of the guide tube 104 extends along the slot 420 between the open bottom 430 and the open top 432.

The slot 420 extends only partially along the handle 106. In particular, the slot 420 opens at a proximal end 124 (FIG. 1) of the handle 106, and the slot terminates prior to the distal end 122 of the handle 106, and thus visible in FIG. 4 is the surface 436 that defines a distal-most portion of the slot 420. In example embodiments, the slot 420 defines a width W4 about the same as the internal diameter ID2 of the guide tube 104. However, in other cases the surfaces 424 and 428 need not be parallel, and thus the slot may widen with increasing distance from the longitudinal central axis 118. The width W4 is selected, designed, and/or constructed based on the diameter of the tack wire to be used with the guide tool. For example, if the tack wire to be used with the guide tool 100 has a diameter of about 1.1 mm, then the width W2 of the slot 420 may be larger than the largest expected diameter tack wire by between 0.1 mm to 1.0 mm, inclusive. For a guide tool 100 for use with tack wires having a diameter of 1.1 mm, the width W2 may range from 1.2 mm to 2.1 mm, inclusive.

In the view of FIG. 4, looking toward the distal end 122 (FIG. 1) of the handle 106, visible is a bore or aperture 434 that is in fluid communication with the guide tube 104 (FIG. 1). For some example offsets O (FIG. 2) of the longitudinal central axes of the delivery tube 102 (FIG. 1) and the guide tube 104 (FIG. 1), the aperture 434 overlaps the counter bore 418 such that the transitional surface created by the counter bore 418 includes a cutout or notch to accommodate the aperture 434. Stated otherwise, the radius of curvature 417 projected across the gap formed by the surfaces 424 and 428 overlaps the inside diameter of the aperture 434, which inside diameter is aligned with the inside diameter ID2 (FIG. 2) of the guide tube 104.

Figure 5:
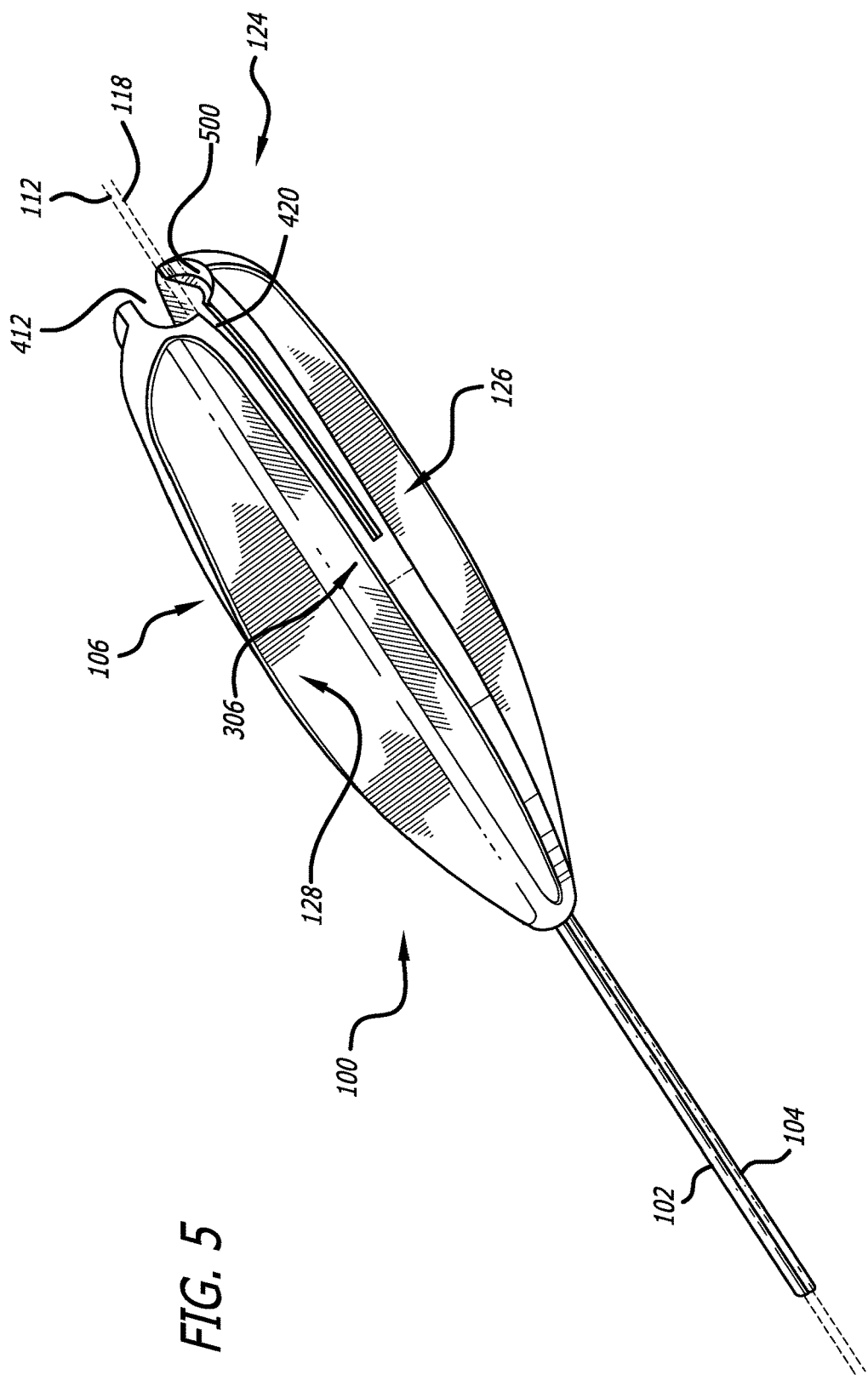
FIG. 5 shows a handle-end perspective view of the guide tool in accordance with at least some embodiments.

FIG. 5 shows a handle-end perspective view of the guide tool 100 in accordance with at least some embodiments. In particular, visible in FIG. 5 is the handle 106 as well as the delivery tube 102 and the guide tube 104. The channel 412 that forms the receptacle 134 is shown to be exposed on the proximal end 124 of the handle 106. The longitudinal central axis 112 is shown extending along and through the bottom of the channel 412. The slot 420 within vane 306 is also shown to be exposed on the proximal end 124 of the handle 106. The longitudinal central axis 118 of the guide tube 104 is shown extending along and through the open bottom of the slot 420. As will be discussed more below, the slot 420 being exposed on the proximal end 124 of the handle 106 enables insertion of tack wires through the guide tool 100 during bone anchor installation. Likewise, the channel 412 being exposed on the proximal end 124 of the handle 106 enables insertion of drill wires and delivery camps through the guide tool 100 during bone anchor installation.

Also visible in FIG. 5 is a counter bore 500 defined at the proximal end 124 of the handle. In particular, the counter bore 500 has a central axis aligned with the longitudinal central axis 112, and has a diameter larger than the width W3 of the channel 412. The counter bore 500 may be used in conjunction with features of the drill guide cartridge and/or the bone anchor cartridge (discussed more below) to help hold the respective cartridges within the receptacle 134. Other mechanisms may be used to hold the respective cartridges within the receptacle, and thus the counter bore 500 may be omitted in some example guide tools 100.

Figure 6:
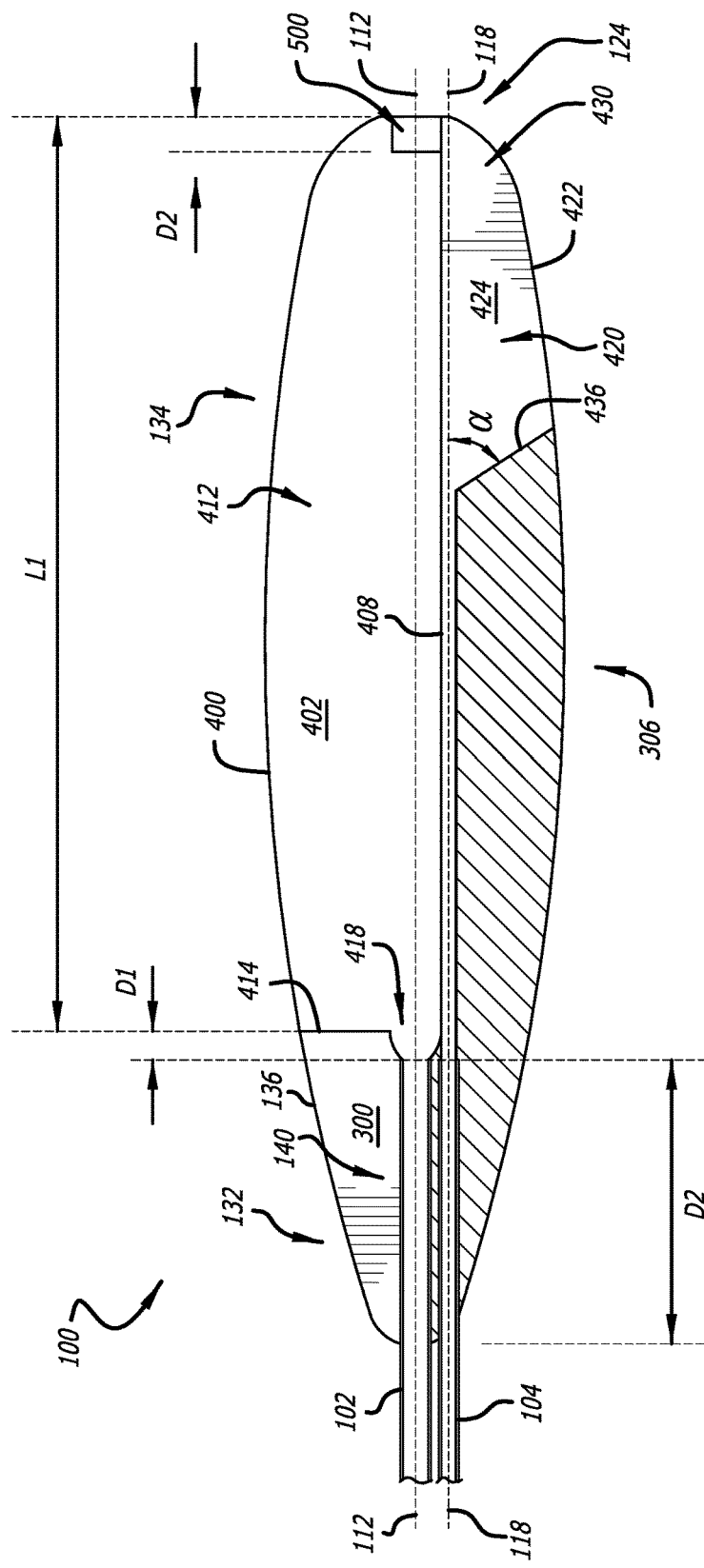
FIG. 6 shows a cross-sectional view of the guide tool in accordance with at least some embodiments.

FIG. 6 shows a cross-sectional view of the guide tool 100 in accordance with at least some embodiments. In particular, the view of FIG. 6 is a cross-sectional view taken along a plane in which both the longitudinal central axis 112 of the delivery tube 102 and the longitudinal central axis 118 of the guide tube 104 reside. Thus, the view of FIG. 6 is cut through the channel 140, the receptacle 134, and the slot 420. The delivery tube 102 extends into the distal end 122 of the handle 106 a distance D1 (e.g., between 10 and 15 mm, inclusive). Because of the cut from the cross-sectional view, visible in FIG. 6 is the surface 300 created by the wall 136 within the channel 140. Shoulder 414 resides between the surface 300 and the surface 402 created by the wall 400. In the view of FIG. 6 the shoulder 414 is perpendicular to the plane of the page. FIG. 6 further shows the longitudinal central axis 112 of the delivery tube 102 extends along channel 412 of the receptacle 134 above the bottom 408. The transition between the bottom 408 and the delivery tube 102 defines a counter bore 418 that transitions between the two features. In the example of FIG. 6, the counter bore 418 defines a bulbous or semi-circular shape, but any suitable shape may be used (e.g., conic frustum). In example cases, the counter bore 418 has a depth D1 of between 1 mm and 6 mm, inclusive, and in a particular case the depth D1 is 3 mm.

Considering now the guide tube 104 and related structures, in example cases the guide tube 104 is aligned with the vane 306. The guide tube 104 also extends into the distal end 122 of the handle 106 a distance D2 (e.g., between 10 and 15 mm, inclusive), though the distance the guide tube 104 extends into the handle 106 need not be the same the distance the delivery tube 102 extends into the handle 106. Because of the cut from the cross-sectional view, visible in FIG. 6 is the surface 424 created by wall 422 within slot 420. In the view of FIG. 6, surface 436 is perpendicular to the plane of the page. In example cases, the surface 436 defines an angle α measured between the longitudinal central axis 118 and the surface 436. In some cases the angle α is an acute angle. In other cases the angle α may be ninety angular degrees, and in yet still other cases the angle α may be an obtuse angle. FIG. 6 further shows the longitudinal central axis 118 of the guide tube 104 extends along slot 420.

Also partially visible in the view of FIG. 6 is the counter bore 500. That is, in the view of FIG. 6 the portion of the counter bore 500 within the surface 402 is shown. The example counter bore may extend a distance D2 into the channel 412, and in some cases the distance D2 may be between 2 mm and 10 mm, inclusive. As will be discussed more below, during insertion of a drill guide cartridge and/or a bone anchor cartridge with a complementary feature, the proximal end 124 may separate slightly to accommodate insertion. Finally, the example receptacle 134 has a length L1 measured from the shoulder 414 to the proximal end 124 of the guide tool 100, which length L1 may be between 5 centimeters (cm) and 15 cm, inclusive, and in some cases between 7 cm and 10 cm, inclusive.

The various embodiments discussed to this point show the longitudinal central axis 112 of the delivery tube 102 and the longitudinal central axis of the handle 106 being coaxial; however, in other cases the longitudinal central axis 118 of the guide tube 104 and the longitudinal central axis of the handle 106 may be coaxial, and in those cases the delivery tube 102 would be offset therefrom.

In example embodiments, the handle 106 may be made from any suitable material, such as acetyl or polyether ether ketone (PEEK). The example handle with vanes reduces the amount of material used to create the handle, and may also help in the curing process. Example embodiments are one time use, disposable items. In order to prevent the guide tool 100 from being re-used (e.g., autoclaved and re-used), in some cases the material that forms the handle 106 has a melting point below the temperature at which an autoclave may operate (e.g., a melting point below 121° Celsius).

The handle 106 may be created in any suitable fashion. For example, the handle 106 may be created by injecting the handle material into a mold or form. In other cases, however, the handle may be milled from a larger billet of solid material (e.g., in a computer-controlled milling machine). While the example handle uses vanes for the reasons discussed above, in other cases the handle may be more cylindrical (e.g., similar to the handle of a screw driver) yet having the various channels, slots, and receptacle areas. Thus, describing a wall that creates a channel or slot shall not be read to require the presence of vanes on the handle. The specification now turns to a drill guide cartridge.

The Drill Guide Cartridge

Figure 7:
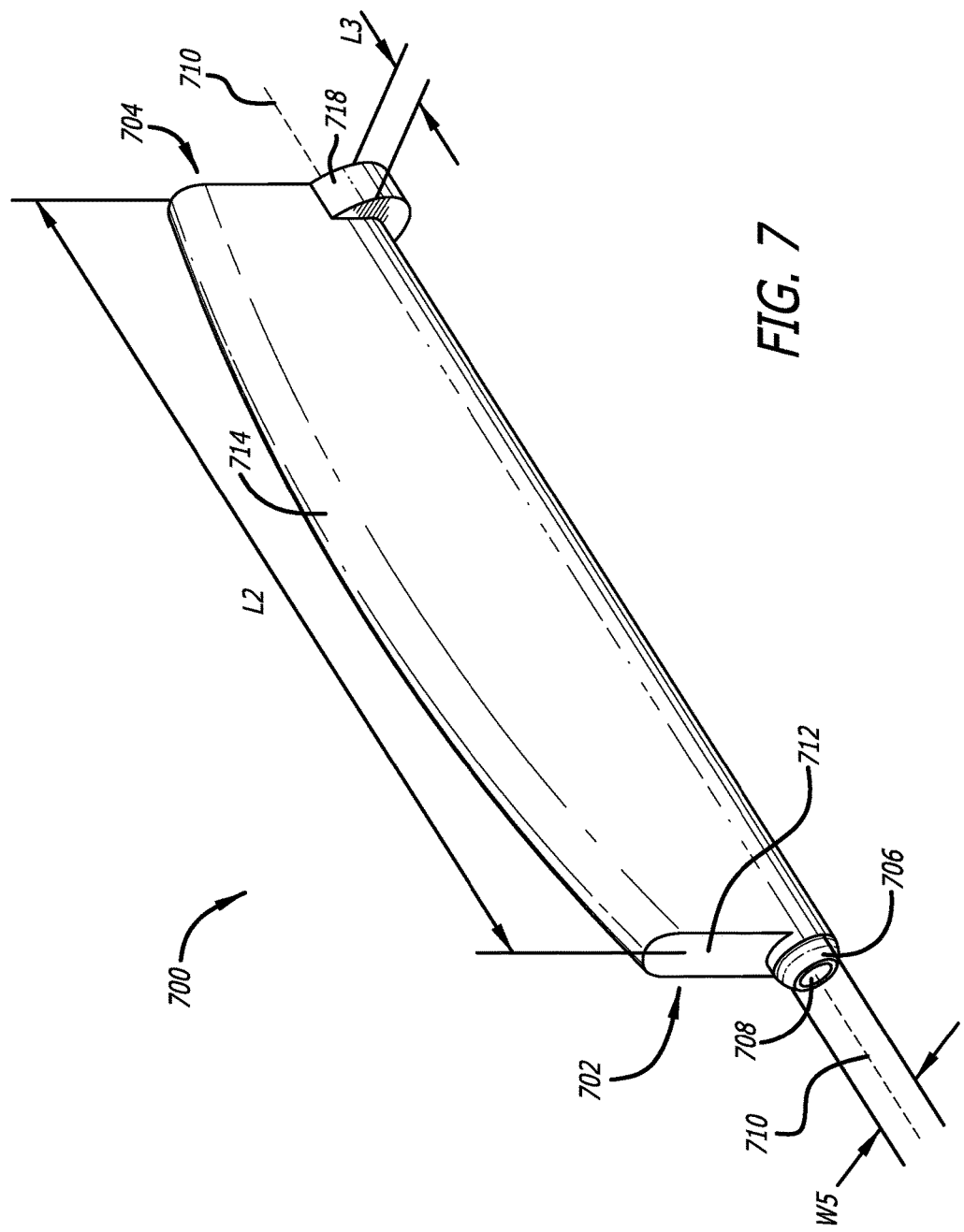
FIG. 7 shows a perspective view of a drill guide cartridge in accordance with at least some embodiments.

Returning briefly to FIG. 1, in accordance with example embodiments various cartridges may be inserted into the receptacle 134. One of those example cartridges is a drill guide cartridge that assists the surgeon in drilling a blind bore or pilot hole into the underlying bone prior to insertion of the first bone anchor. FIG. 7 shows a perspective view of a drill guide cartridge 700 in accordance with at least some embodiments. In particular, the example drill guide cartridge 700 defines a distal end 702 and a proximal end 704. Defined on the distal end 702 is a tab or projection 706 that extends outward from the drill guide cartridge 700. The example projection 706 is shown as bulbous, but the projection 706 may take any suitable shape (e.g., conic frustum, right circular cylinder). The projection 706 defines an aperture 708 that leads to a passageway or delivery lumen that extends the length of the drill guide cartridge 700. The lumen defines a longitudinal central axis 710. When the drill guide cartridge 700 is installed within the receptacle 134 (FIG. 1) the guide tool 100 (FIG. 1), the projection 706 telescopes within the counter bore 418 (FIG. 4) to help hold the distal end 702 of the drill guide cartridge 700 within the receptacle, and to make the longitudinal central axis 710 coaxial with the longitudinal central axis 112 (FIG. 1) of the guide tube 104 (FIG. 1).

The example drill guide cartridge 700 defines a length L2 from the front surface 712 to the distal end 702 (e.g., not including the length of the projection 706). In example cases the length L2 is the same as or longer than the length L1 (FIG. 6) of the receptacle 134. Thus, the length L2 may be between 5 cm and 15 cm, inclusive, and in some cases between 7 cm and 10 cm, inclusive. The example drill guide cartridge 700 defines an outer surface 714 that is arched or rounded lengthwise, for example, rounded to match the vane 130 (FIG. 1) in which the receptacle 134 is defined. In other cases, the outer surface 714 need not match the vane 130.

The example drill guide cartridge 700 further defines a projection or flange 718 disposed at the proximal end 704 and that extends outward from the drill guide cartridge 700. The example flange 718 is shown as a partial right circular cylinder having a length L3 (measured parallel to the longitudinal central axis 710). In accordance with example embodiments, the length L3 is about the same as the distance D2 (FIG. 6) of the counter bore 500 (also FIG. 6). The flange 718 is selected, designed, and/or constructed to fit within the counter bore 500 at the proximal end 124 of the guide tool 100. The flange 718 and the counter bore 500 thus act to lock the proximal end 704 of the drill guide cartridge 700 into the receptacle of the guide tool 100, while the projection 706 locks the distal end 702 of the drill guide cartridge 700 within the receptacle.

Figure 8:
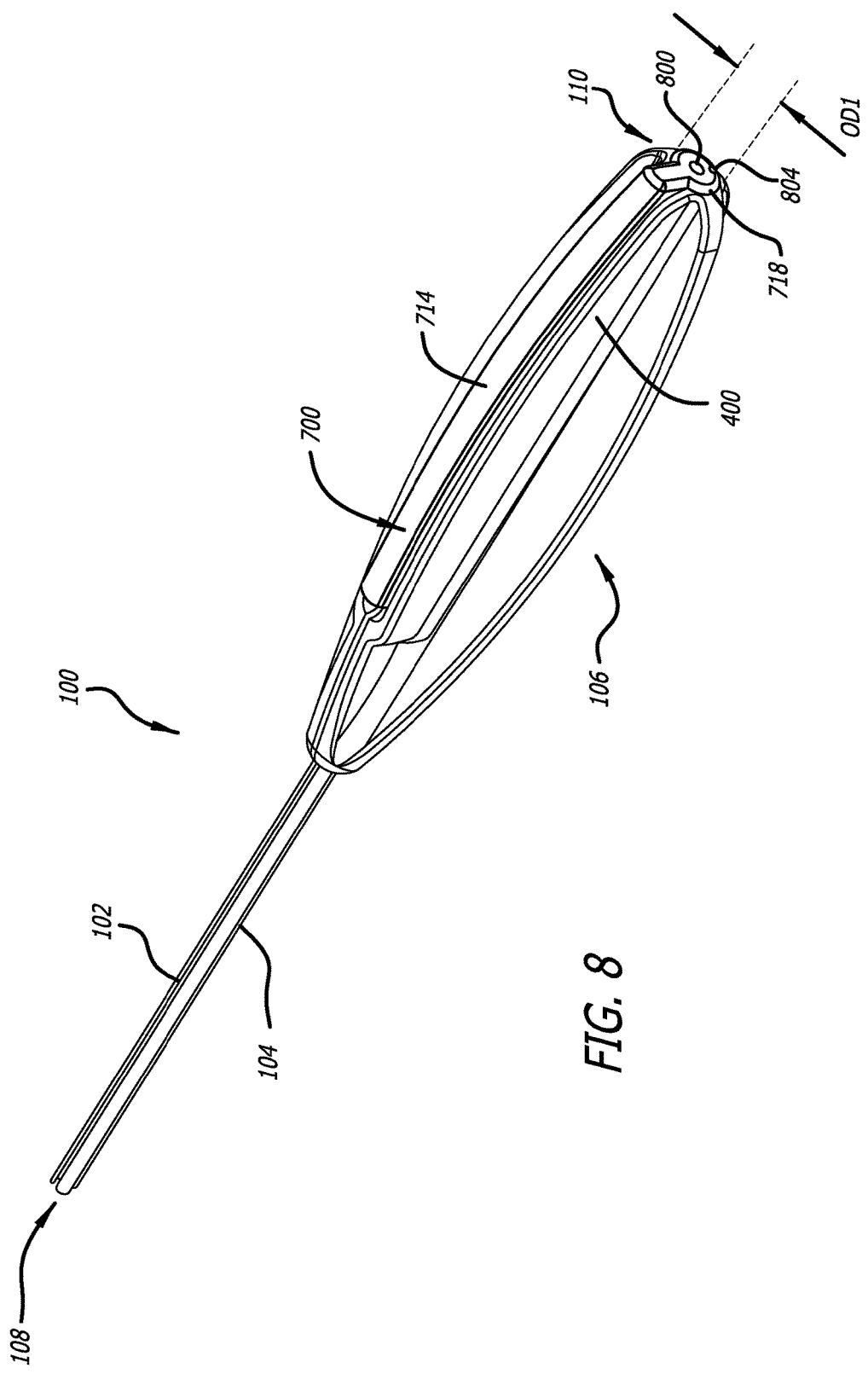
FIG. 8 shows a perspective view of the guide tool with the drill guide cartridge installed, in accordance with at least some embodiments.

FIG. 8 shows a perspective view of the guide tool with the drill guide cartridge installed, in accordance with at least some embodiments. In particular, the view of FIG. 8 is a perspective view from the proximal end 110 of handle 106 looking toward the distal end 108 of the guide tool 100. Visible in FIG. 8 are the delivery tube 102, the guide tube 104, the handle 106, along with the drill guide cartridge 700 installed within the receptacle of the handle 106. Better shown in FIG. 8 is the flange 718, including an aperture 800 defined within the flange. The aperture 800 leads to the lumen that runs through the drill guide cartridge 700. FIG. 8 shows a notch 804 at the bottom of the flange 718, opposite the outer surface 714. As will be discussed more below, the notch 804 enables insertion of a tack wire prior to drilling, while the aperture 800 and the lumen through the drill guide cartridge 700 enable telescoping a drill wire through the guide tool 100 for creation of the blind bore into the underlying bone for an example tissue repair. Finally, the circular portion of the flange 718 defines an outside diameter OD1 (measured perpendicular to the longitudinal central axis of the lumen). The outside diameter OD1 is selected, designed, and/or constructed to create an interference fit with an inside diameter of the counter bore 500 (FIG. 5) of the handle 106. Thus, in one example embodiment the outside diameter OD1 of the flange 718 is the same as or slightly larger than an inside diameter of the counter bore 500. When the flange 718 is telescoped within the counter bore 500, the walls 400 and 404 of the receptacle may separate slightly (e.g., 0.1 mm or less) to create the interference fit. The description now turns to an example bone anchor cartridge.

The Anchor Cartridge with Two Bone Anchors

During example surgical procedures, bone anchors may be installed into a bone region underlying a tissue to be repaired. In accordance with example embodiments, the bone anchors and the suture lines are installed using the guide tool 100. Though an example surgical procedure will be discussed in greater detail below, for now consider that a blind bore into the bone (in some cases through the tissue) is created using a drill wire telescoped through the drill guide cartridge 700 and thus through the delivery tube 102. Once the blind bore is created, the drill wire is removed, and likewise the drill guide cartridge 700 is removed from the handle 106 of the guide tool 100. The bone anchor to be installed in the blind bore comes pre-installed in a bone anchor cartridge (hereafter just "anchor cartridge" to avoid confusion) that is installed in the guide tool 100.

Figure 9:
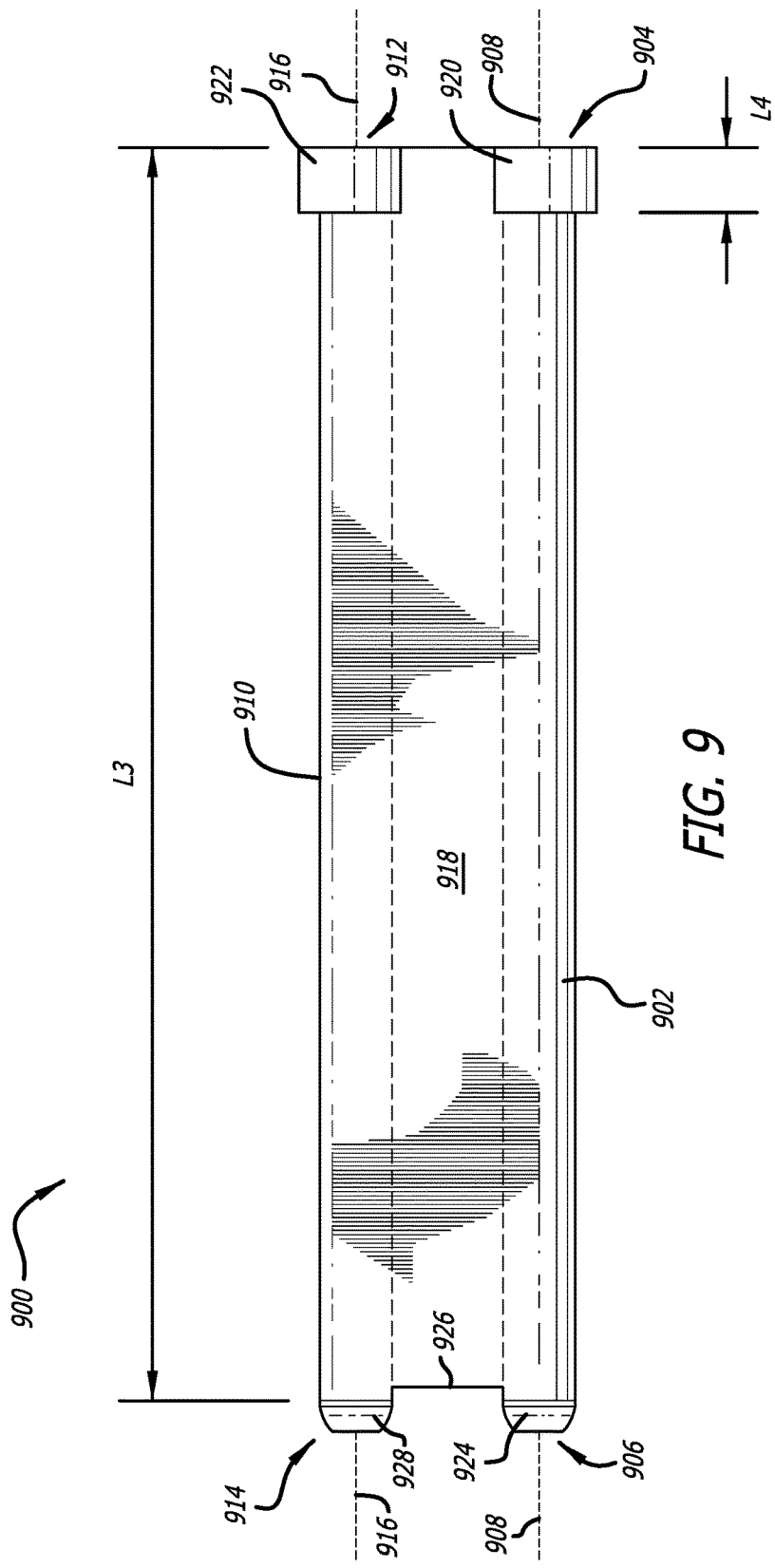
FIG. 9 shows a side elevation view of an anchor cartridge, in accordance with at least some embodiments.

FIG. 9 shows a side elevation view of an anchor cartridge in accordance with at least some embodiments. In particular, the anchor cartridge 900 defines a tube 902 defining a proximal end 904, a distal end 906, and a central axis 908. The anchor cartridge 900 further defines a tube 910 defining a proximal end 912, a distal end 914, and a central axis 916. The central axis 916 of the tube 910 is parallel to and offset from the central axis 908 of the first tube.

The example anchor cartridge 900 further includes a side wall or spacer 918. In example cases there is a smooth transition between an outside diameter of each tube 902 and 910 and the spacer 918, and thus the spacer in FIG. 9 is defined approximately between the dashed lines shown. A second spacer, not visible in FIG. 9, resides on the opposite side of the bone anchor cartridge, and is discussed more below.

The example anchor cartridge 900 further defines a projection or flange 920 disposed at the proximal end 904 of the tube 902. The flange 920 extends outward from the anchor cartridge 900. The example flange 920 is shown as a partial right circular cylinder having a length L4 (measured parallel to the central axis 908). In accordance with example embodiments, the length L4 is about the same as the distance D2 (FIG. 6) that the counter bore 500 (also FIG. 6) extends into the handle. The flange 920 is selected, designed, and/or constructed to fit within the counter bore 500 at the proximal end 124 of the guide tool 100. The flange 920 and the counter bore 500 thus act to lock or hold the proximal end 904 of the anchor cartridge 900 in the receptacle of the guide tool 100 when tube 902 of the anchor cartridge 900 is installed within the receptacle 134 (FIG. 1) of the handle 106 (FIG. 1).

The example anchor cartridge 900 further defines a projection or flange 922 disposed at the proximal end 912 of the tube 910. The flange 922 extends outward from the anchor cartridge 900. The example flange 922 is shown as a partial right circular cylinder having a length the same as flange 920, but in other cases the length of flange 922 need not be the same as flange 920. The flange 922 is selected, designed, and/or constructed to fit within the counter bore 500 (FIG. 5) at the proximal end 124 of the guide tool 100 (FIG. 1). The flange 922 and the counter bore 500 thus act to lock or hold the proximal 912 of the anchor cartridge 900 in the receptacle 134 (FIG. 1) of the guide tool 100 when tube 910 of the anchor cartridge 900 is installed within the receptacle 134 (FIG. 1). It follows that in use the anchor cartridge 900 is installed into the receptacle 134 in one of two orientations: one orientation with the tube 902 within the channel 412 (FIG. 4) that defines the receptacle 134, and the tube 902 coaxial with the delivery tube 102 (FIG. 1); and a second orientation with the tube 910 within the channel 412 that defines the receptacle 134, and the tube 910 coaxial with the delivery tube 102. An example surgical method where the anchor cartridge 900 is installed in both orientations is discussed more below.

Still referring to FIG. 9, the example anchor cartridge 900 further defines a projection 924 at distal end 906 of the tube 902. The projection 924 extends beyond a distal end 926 the spacer 918. Another projection 928 is defined at the distal end 914 of the tube 910. The projection 928 extends beyond the distal end 926 of the spacer 918. In the example shown in FIG. 9, the projections are bulbous or hemispherical. However, the projections 924 and 928 may take any suitable form, such as conical or conic frustums.

Figure 10:
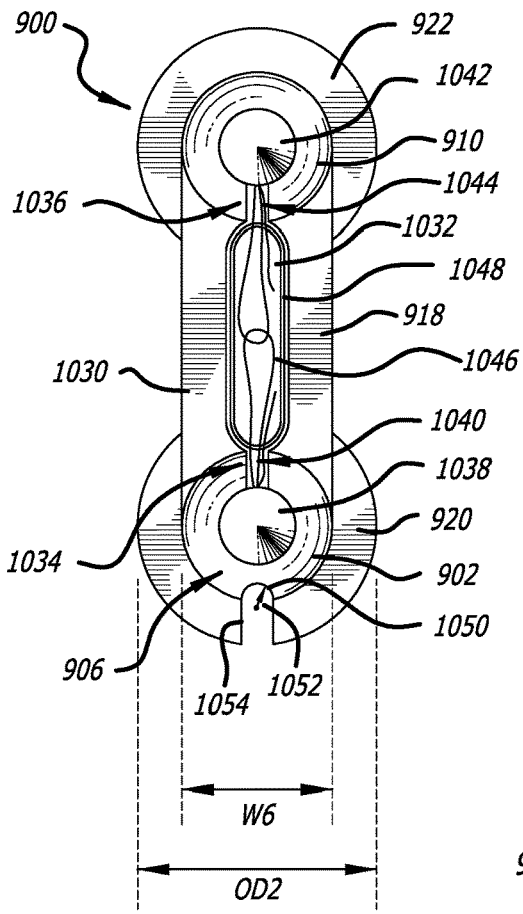
FIG. 10 shows an end-elevation view of the distal end of the anchor cartridge, in accordance with at least some embodiments.

FIG. 10 shows an end-elevation view of the anchor cartridge 900, in accordance with at least some embodiments. In particular, visible in FIG. 10 are the tube 902, the tube 910, the spacer 918 separating the tubes 902 and 904, the flange 920 associated with the tube 902, and the flange 922 associated with the tube 910. Also visible in FIG. 10 is the second wall or spacer 1030. The spacer 1030 is parallel to the spacer 918. The spacer 1030 is coupled to the tube 902 and the tube 910. The spacers 918 and 1030 define a suture volume 1032 between them.

In accordance example embodiments, the tube 902 defines a slot 1034 open to and extending from the distal end 906 to the proximal end 904 (not visible in FIG. 10). The slot 1034 creates a fluid communication channel between an inside diameter of the tube 902 and the suture volume 1032. Similarly, the tube 910 defines a slot 1036 open to and extending from the distal end 914 to the proximal end 912 (not visible in FIG. 10). The slot 1036 thus creates a fluid communication channel between an inside diameter of the tube 910 and the suture volume 1032.

Also visible in FIG. 10 are end views of two bone anchors. In particular, a bone anchor 1038 is disposed within the tube 902. A suture line 1040 is tied to a proximal end (not visible) of the bone anchor 1038, and the suture line 1040 extends through the slot 1034 of the tube 902 into the suture volume 1032. Similarly, a bone anchor 1042 is disposed within the tube 910. A suture line 1044 is tied to a proximal end (not visible) of the bone anchor 1042, and the suture line 1044 extends through the slot 1036 of the tube 910 into the suture volume 1032. In accordance with at least some embodiments, the suture lines 1040 and 1044, after extending through the slots 1034 and 1036, respectively, are disposed within an internal volume 1046 of a suture sleeve 1048.

Still referring to FIG. 10, the example anchor cartridge 900 defines a width W6 (measured perpendicular to the central axis 908 or central axis 916). The width W6 may be measured across the outside diameter of either tube 902 or 910, or the width W6 may be measured across outer faces of the spacers 918 and 1030. Inasmuch as the anchor cartridge 900 is intended to fit within the receptacle 134 (FIG. 1) of the guide tool 100 (FIG. 1), the width W6 is slightly smaller than the width W3 (FIG. 4) of the channel 412 (FIG. 4) that defines the receptacle 134. For example, the width W6 may be between 0.01 and 0.1 mm, inclusive, smaller than the width W3 to enable the anchor cartridge 900 to telescope within the receptacle 134. Further shown in FIG. 10, the circular portions of flange 920 define an outside diameter OD2 (measured perpendicular to the central axis 908) greater than the width W6. The same is true regarding flange 922 and tube 910. The outside diameter OD2 of the flanges are selected, designed, and/or constructed to create an interference fit with an inside diameter of the counter bore 500 (FIG. 5) of the handle 106 (FIG. 1). Thus, in one example embodiment the outside diameter OD2 is the same as or slightly larger than an inside diameter of the counter bore 500 (FIG. 5). When the flange 920 or flange 922 is telescoped within the counter bore 500, the walls 400 and 404 of the receptacle may separate slightly (e.g., 0.1 mm or less) to enhance the interference fit.

The example anchor cartridge 900, and specifically the tube 902, further defines a trough 1050 with an open top and a closed bottom. The trough 1050 opening outward at a radial direction or radial location opposite the slot 1034 of the tube 902. When the anchor cartridge 900 is installed within the receptacle 134 (FIG. 1) of the handle 106 (FIG. 1), the closed bottom of the trough 1050 defines a radius of curvature 1052 with a center that resides on the longitudinal central axis 118 (FIG. 1) of the guide tube 104 (FIG. 1, and see also FIG. 4). The trough 1050 runs from the proximal end 904 (not visible) of the tube 902 to the distal end 906 parallel to the central axis 908. The flange 920 has a corresponding notch 1054 with an open top and closed bottom. The trough 1050 is aligned with the notch 1054. For reasons that will become more clear below, in example embodiments the trough 1050 and notch 1054 are present in only one tube/flange set (here the tube 902 and the flange 920), but in other cases the second tube/flange set (tube 910 and flange 922) may also include similar trough and notch. In yet still other cases, the spacing or offset between the delivery tube 102 (FIG. 1) and the guide tube 104 (FIG. 1) may be large enough that the trough can be omitted from the tube 902, though the notch 1054 may be still be present.

The tube 902 and tube 910, particularly the outer surfaces of the tube 902 and the tube 910 not "covered" or abutting by the spacers 918 and 1030, each define semi-circular regions. Referring simultaneously to FIGS. 4 and 10, the bottom 408 of the channel 412 that at least partially defines the receptacle 134 is curved and has the radius of curvature 417. The semi-circular regions of the outer surfaces of the tube 902 and the tube 910 are thus a negative image of the bottom 408. However, other shapes are possible for the bottom 408 as discussed above, and the outer surfaces of the tubes 902 and 910 need only be able to fit within the bottom 408. In some cases the outer surfaces of the tubes 902 and 910 will be negative images of the bottom 408, but in other cases the partial cross-sectional shapes need not match For example, the bottom 408 may be a flat surface perpendicular to the surfaces 402 and 406, and yet the outer surfaces of the tube 902 and the tube 910 may be any suitable shape, such as flat or semi-circular. Similarly for the flanges 920 and 922, while shown as right circular cylinders, the flanges 920 and 922 may take any suitable cross-sectional shape that fits within the counter bore 500 (FIG. 5), and the cross-sectional shapes of the flanges need not match the cross-sectional shape of the counter bore 500.

Figure 11:
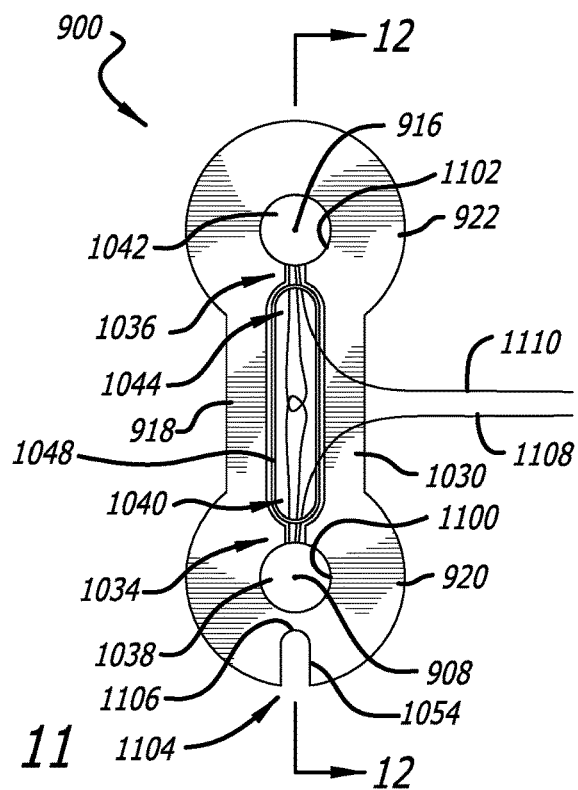
FIG. 11 shows an end-elevation view of the proximal end of the anchor cartridge, in accordance with at least some embodiments.

FIG. 11 shows an end-elevation view of the proximal end of the anchor cartridge, in accordance with at least some embodiments. In particular, visible in FIG. 11 are the flange 920 at the bottom of the figure, and the flange 922 at the top of the figure. Between the two flanges 920 and 922 are portions of the spacers 918 and 1030. Flange 920 defines an aperture 1100 that is circular, and the central axis of the aperture is coaxial with the central axis 908 of the tube 902 (the central axis 908 is perpendicular to the plane of the page, and thus shown as a dot). Flange 922 defines an aperture 1102 that is circular, and the central axis of the aperture 1102 is coaxial with the central axis 916 of the tube 910 (the central axis 916 is perpendicular to the plane of the page, and thus shown as a dot). Further visible in FIG. 11 is the notch 1054 in the flange 920. The notch 1054 defines an open top 1104 and a closed bottom 1106. The notch 1054 is shown to open outward a radial location or radial direction opposite the location of the slot 1034. The flange 922 of the example anchor cartridge 900 does not have a corresponding notch, but in other cases the flange 922 may also have a corresponding notch.

Visible through the apertures 1100 and 1102 are the bone anchors 1038 and 1042, respectively. Further visible in FIG. 11 is the fact the slots 1034 and 1036 are open on the proximal end of the anchor cartridge 900. More particularly, the slot 1034 provides fluid communication between the internal volume of the tube 902 and the internal volume 1046 of the defined between spacer 918 and the spacer 1030. Similarly, the slot 1036 provides fluid communication between the internal volume of the tube 910 and the internal volume 1046 of the defined between spacer 918 and the spacer 1030. Further visible in FIG. 11 are the suture line 1040, the suture line 1044, and the suture sleeve 1048, all within the internal volume 1046. The suture line 1040 includes a bitter end or tightening line 1108, and the suture line 1044 include a bitter end or tightening line 1110. The use of tightening lines 1108 and 1110 is discussed more below in relation to tightening the suture over to and against tissue.

Figure 12:
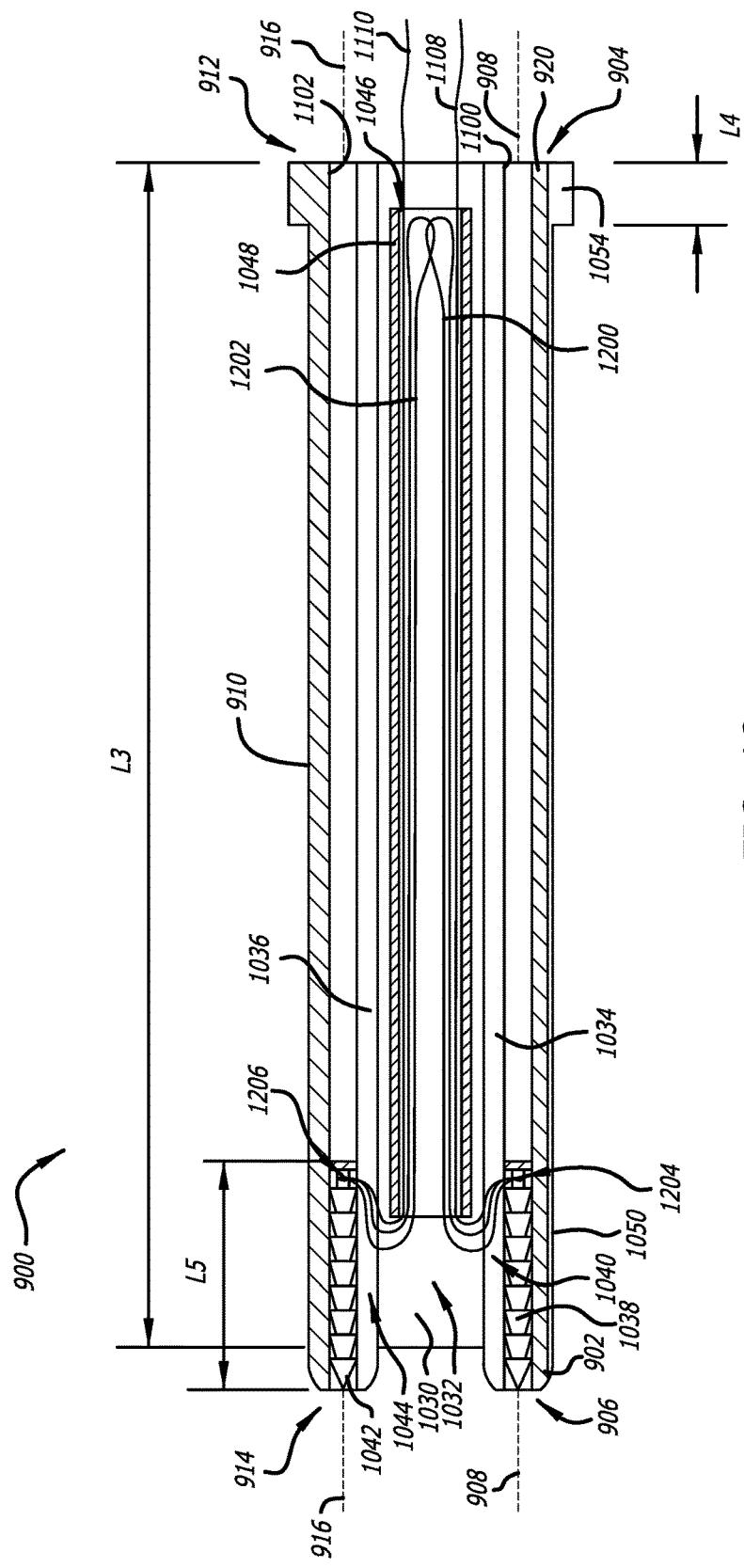
FIG. 12 is cross-sectional view of the anchor cartridge taken substantially along lines 12-12 of the FIG. 11, and in accordance with at least some embodiments.

FIG. 12 shows a cross-sectional view of the anchor cartridge taken substantially along lines 12-12 of the FIG. 11, and in accordance with at least some embodiments. In particular, visible on the a lower portion of the tube 902 is a portion of the trough 1050 running the length of the tube 902 parallel to the central axis 908 of the tube 902. Similarly, visible on a lower portion of the flange 920 is a portion of the notch 1054. The cross-sectional view of FIG. 12 cuts through the middle of the trough 1050 and the middle of the notch 1054, and so what is seen is one side wall of the trough 1050 and one side wall of the notch 1054. The tube 902 defines an inside diameter running from the proximal end 904 to the distal end 906. The inside diameter of tube 902 is exposed on the distal end 906 by way an aperture, and the inside diameter of the tube 902 is exposed on the proximal end 904 by way of aperture 1100. The tube 902 couples to the spacer 1030 on the back side of the view of FIG. 12. Between the inside diameter of the tube 902 and the suture volume 1032 is the slot 1034 (only one wall of which is visible in the cross-sectional view of FIG. 12).

Tube 910 is likewise shown on an upper portion of FIG. 12. The tube 910 defines an inside diameter running from the proximal end 912 to the distal end 914. The inside diameter of tube 910 is exposed on the distal end 914 by way an aperture, and the inside diameter of the tube 910 is exposed on the proximal end 912 by way of aperture 1102. The tube 910 couples to the spacer 1030 on the back side of the view of FIG. 12. Between the inside diameter of the tube 910 and the suture volume 1032 is the slot 1036 (only one wall of which is visible in the cross-sectional view of FIG. 12).

Bone anchor 1038 is disposed within the inside diameter of the tube 902. The suture line 1040 is tied to a proximal end of the bone anchor 1038, and the suture line 1040 extends through the slot 1034 into the suture volume 1032. Bone anchor 1042 is disposed within the inside diameter of the tube 910. The suture line 1044 is tied to a proximal end of the bone anchor 1042, and the suture line 1044 extends through the slot 1036 of the second tube into the suture volume 1032.

The bone anchor 1042 in the tube 910 has a length L5 (measured along the central axis 916). In some cases, the bone anchor 1038 in the tube 902 has the same length L5 (measured along central axis 908), but in other cases the bone anchors need not have the same length. The tube 910 has the length L3 previously discussed. In some example cases the length L3 of the tube 910 is at least twice the length L5 of the bone anchor 1042, and in some cases at least four times the length L5 of the bone anchor 1042. The tube 902 has the length L3 as previously discussed, and thus in some cases the length L3 of the tube 902 is at least twice the length L5 of the bone anchor 1038, and in some cases at least four times the length L5 of the bone anchor 1038. Having the length of the tubes 902 and 910, and thus the length of the anchor cartridge 900, longer than the bone anchors enables a sufficient length of the suture volume 1032 to hold the suture lines 1040 and 1044 within the suture volume 1032, which may reduce fouling of the suture lines.

The example bone anchors 1038 and 1042 are shown within the tubes 902 and 910, respectively. More specifically, the example bone anchors 1038 and 1042 are shown fully within the internal diameters or their respective tubes. However, in other embodiments the bone anchors may protrude slightly out of the tubes. Speaking to bone anchor 1038 as representative of both, the distal end of the bone anchor 1038 may protrude outside the tube 902 beyond the projection 924.

Disposed within the suture volume 1032 is the suture sleeve 1048, also shown in cross-section. The suture sleeve 1048 defines an internal volume 1046, within which the suture lines are disposed. The suture sleeve 1048 may take any suitable form, such as a sleeve of plastic material (e.g., acetyl, PEEK). The suture lines enter the suture sleeve 1048 on the distal end of the suture sleeve, and a portion of each the suture line may extend out of the proximal end of the suture sleeve 1048. In particular, the suture line 1040 comprises a slipknot defining a loop 1200 and the tightening line 1108, The loop 1200 is disposed within the interior volume 1046 of the suture sleeve 1048. The tightening line 1108 extends through the interior volume 1046 of the suture sleeve 1048 and has a terminal end outside the suture sleeve 1048. Similarly, suture line 1044 comprises a slipknot defining a loop 1202 and the tightening line 1110. The loop 1202 is disposed within the interior volume 1046 of the suture sleeve 1048 and looped through the loop 1200. The tightening line 1110 extends through the interior volume 1046 of the suture sleeve 1048 and has a terminal end outside the suture sleeve 1048. In the example embodiment shown, and with the exception of the tightening lines 1108 and 1110, the suture lines 1040 and 1044 reside within the suture volume 1032. However, in other embodiments the suture sleeve, as well as the suture lines 1040 and 1044, may extend outward at the proximal end of the anchor cartridge 900.

In accordance with example embodiments, the suture sleeve 1048 may provide suture management within the anchor cartridge 900 during installation of the bone anchors. More particularly, the suture sleeve 1048 holds the various features of the suture lines within the suture volume 1032 to reduce interference or contact of the suture lines with various other devices, such as the drill wires used to create the pilot holes in the bone, and/or the delivery camps used to push the bone anchors into the pilot holes. The length L3 of the tubes 902 and 910, and correspondingly the length of the suture sleeve 1048, may be selected such that the length of travel of the first bone anchor placed (likely bone anchor 1038 in the tube 902) from the anchor cartridge 900 pulls the loop 1200 fully or partially out of the anchor cartridge 900, but leaves some or all the loop 1202 within the anchor cartridge 900 (and specifically within the suture sleeve 1048). In example embodiments, enough "slack" remains in the loop 1202 to remove the anchor cartridge from the guide tool 100 (FIG. 1) and then re-install the anchor cartridge 900 within the guide tool 100 such that the tube 910 and thus bone anchor 1042 are aligned with the delivery tube 102 (FIG. 1).

It follows that the loop 1200 is defined by a length of the suture line 1040 measured from a first slipknot 1204 on a bollard of the bone anchor 1038, and the length of the suture line 1040 of the first loop 1200 is longer than the length of the tube 902. Similarly, the loop 1202 is defined by a length of the suture line 1044 measured from a slipknot 1206, and the length of the suture line 1044 of the loop 1202 is longer than the length of the tube 910.

Example Methods of Connecting Tissue to Bone

The specification now turns to an example method of connecting tissue to bone utilizing the guide tool 100, the drill guide cartridge 700, and anchor cartridge 900 described above. In particular, the various example embodiments were developed in the context of repair of a rotator cuff injury in which tendons or muscles in the shoulder have torn or separated from the upper head of the humerus. The example methods that follow are based on the developmental context, but should not be construed as a limitation of the applicability of the various devices. In many cases, the reattachment of the tissue may take place arthroscopically. Thus, several additional instruments and systems may be present, including systems to pump saline into the joint to distend the joint and carry away blood and tissue fragments, and a visualization cannula that provides a view into the region of the repair. The various devices and systems used to implement arthroscopic procedures are not shown so as not to unduly complicate the discussion.

Figure 13:
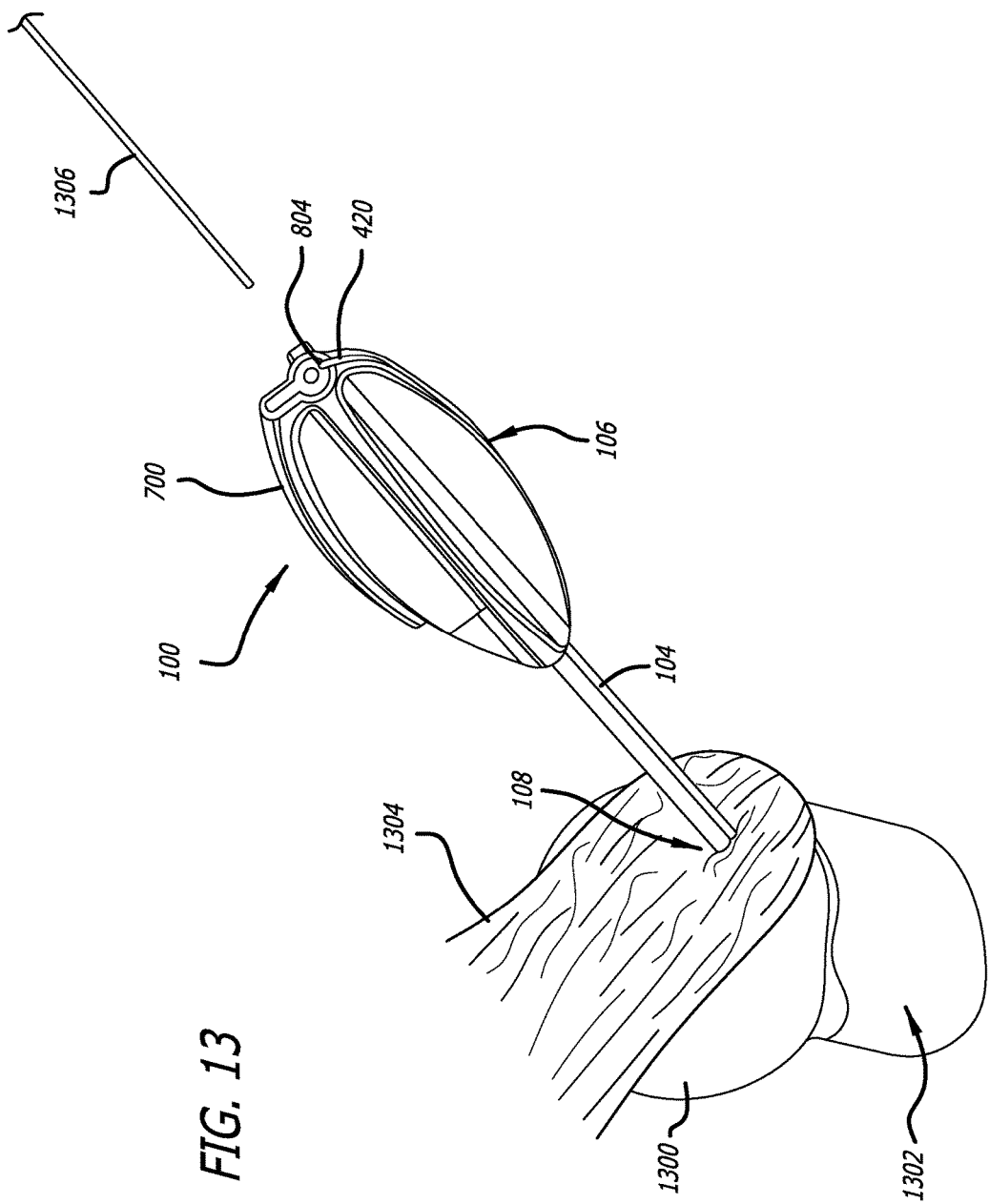
FIG. 13 shows a perspective view of a guide tool in relationship to the upper head of a humerus, in accordance with at least some embodiments.

FIG. 13 shows a perspective view of the guide tool in relationship to the upper head of a humerus, in accordance with at least some embodiments. In particular, visible in FIG. 13 is the guide tool 100 including the drill guide cartridge 700 installed therein, an upper head 1300 of a humerus 1302, and an example tissue 1304 that needs to be re-attached to the upper head 1300 of the humerus 1302, and a tack wire 1306. The tissue 1304 may be, for example, the supraspinatus that has separated from the upper head 1300. The tack wire 1306 in example embodiments is metallic and has a diameter of 1.1 mm. In some cases, the tack wire 1306 has a spade or trocar tip (not specifically shown). The tack wire 1308 has a length (not specifically delineated in the figure) that is longer than the length of the guide tool 100 (e.g., the length measured along the longitudinal central axis 112 (FIG. 1)).

The example method may start by pulling the tissue 1304 in place over a bone location, such as the greater tuberosity of the upper head 1300 of the humerus 1302. The various instruments that may be used to pull and hold the tissue 1304 in place are not shown so as not to further complicate the figure and the discussion. With the tissue 1304 held in place over the bone location, the distal end 108 of the guide tool 100 is abutted against the tissue 1304 at a first location.

With the distal end 108 abutting the tissue 1304 at the first location, the tack wire 1306 is telescoped through the guide tube 104 of the guide tool 100. In particular, the tack wire 1306 is telescoped through the notch 804 of the drill guide cartridge 700, through handle 106, through the guide tube 104, and abutted against the tissue 1304. The tack wire 1306 is then rotated to cut or drill through the tissue 1304, and then cut or drill into the underlying bone. One example purpose of the tack wire is to help hold the distal end 108 of the guide tool 100 in place during bone anchor placement, and thus the depth that the tack wire penetrates into the underlying bone need only be enough to hold the guide tool 100 in place (e.g., between 2 mm to 10 mm, inclusive). Once the distal end of the tack wire 1306 is within the bone, the proximal end of the tack wire 1306 is bent into the slot 420 within the handle 106.

Figure 14:
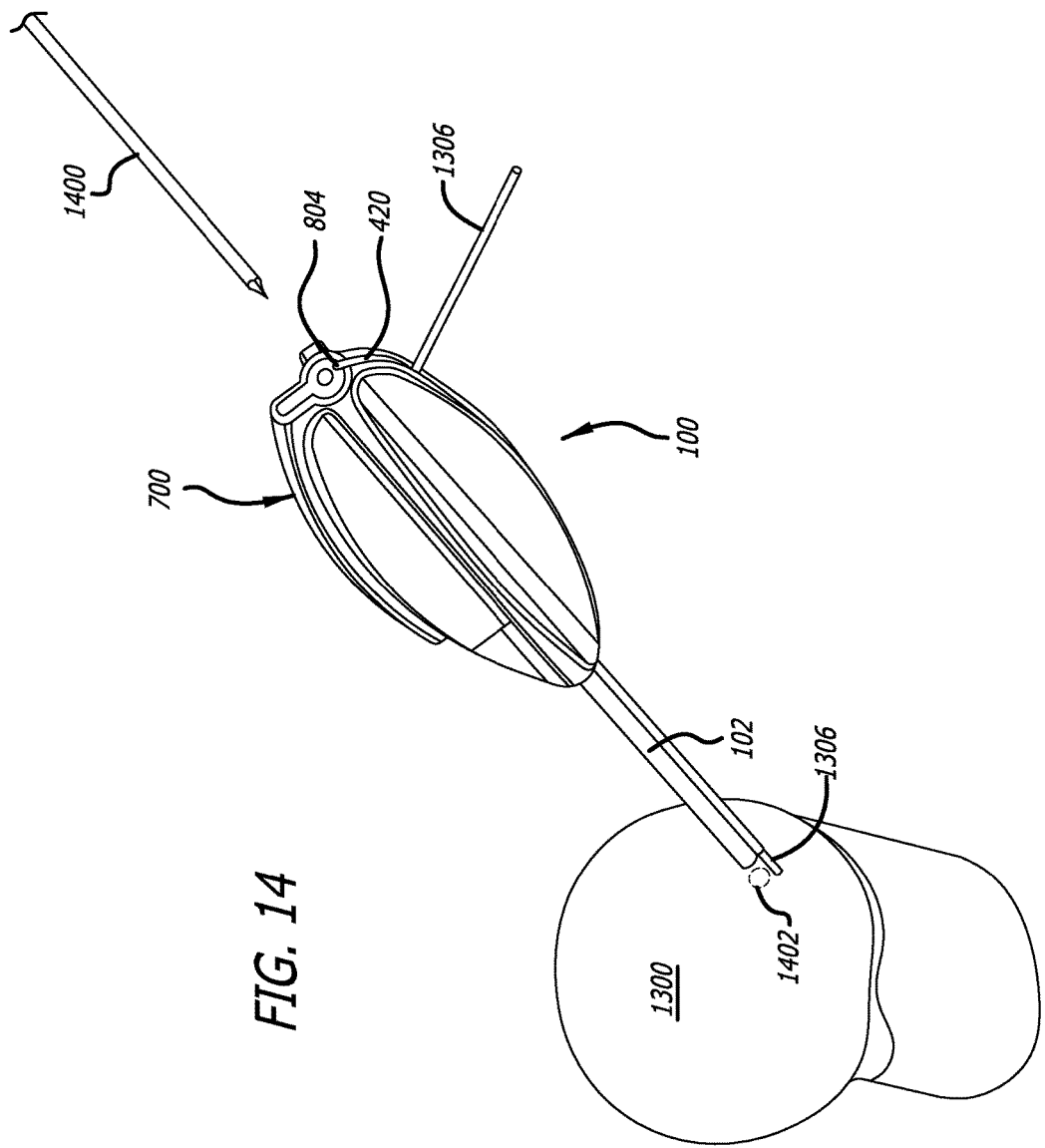
FIG. 14 shows a perspective view of the guide tool in relationship to the upper head of the humerus, in accordance with at least some embodiments.

FIG. 14 shows a perspective view of the guide tool in relationship to the upper head of the humerus, in accordance with at least some embodiments. In particular, the view of FIG. 14 is similar to the view of FIG. 13, but the tissue 1304 has been omitted for purposes of discussion. FIG. 14 shows the proximal end of the tack wire 1306 bent into the slot 420 within the handle 106. Moreover, with the tissue omitted the distal end of the tack wire 1306 extending into the bone is visible. The tack wire 1306 extending into the bone holds the guide tool 100 in place around an axis defined by the tack wire 1306. When the tack wire 1306 is bent into the slot 420, the tack wire 1306 also holds the guide tool 100 against rotation about the tack wire 1306. Thus, the guide tool 100 is held in a fixed location and held in a fixed rotational orientation.

Further visible in FIG. 14 is a drill bit or drill wire 1400. The drill wire 1400 in example embodiments is metallic and has a diameter of 2.0 mm. In some cases, the drill wire 1400 has a spade or trocar tip (not specifically shown). The drill wire 1400 has a length (not specifically delineated in the figure) that is longer than the sum of the length of the guide tool 100 and an expected depth of a pilot hole into which the bone anchor will be installed. The next step in the example method is telescoping the drill wire 1400 though the delivery tube 102 of the guide tool 100. In particular, the drill wire 1400 is telescoped through the aperture 800 of the drill guide cartridge 700. The aperture 800 and drill guide cartridge 700 direct the drill wire 1400 into the delivery tube 102 to abut the tissue at the distal end 108 of the guide tool 100. The drill wire 1400 is then rotated to cut or drill through the tissue, and then cut or drill into the underlying bone. Thus, the distal end of the drill wire 1400 is used to create a blind bore or pilot hole in the bone. The example pilot hole 1402 is shown in dashed lines in FIG. 14. Thereafter, the drill wire 1400 is extracted or removed from the guide tool 100. The next step in the example process is telescoping or driving a bone anchor through the delivery tube 102 into the pilot hole 1402.

Figure 15:
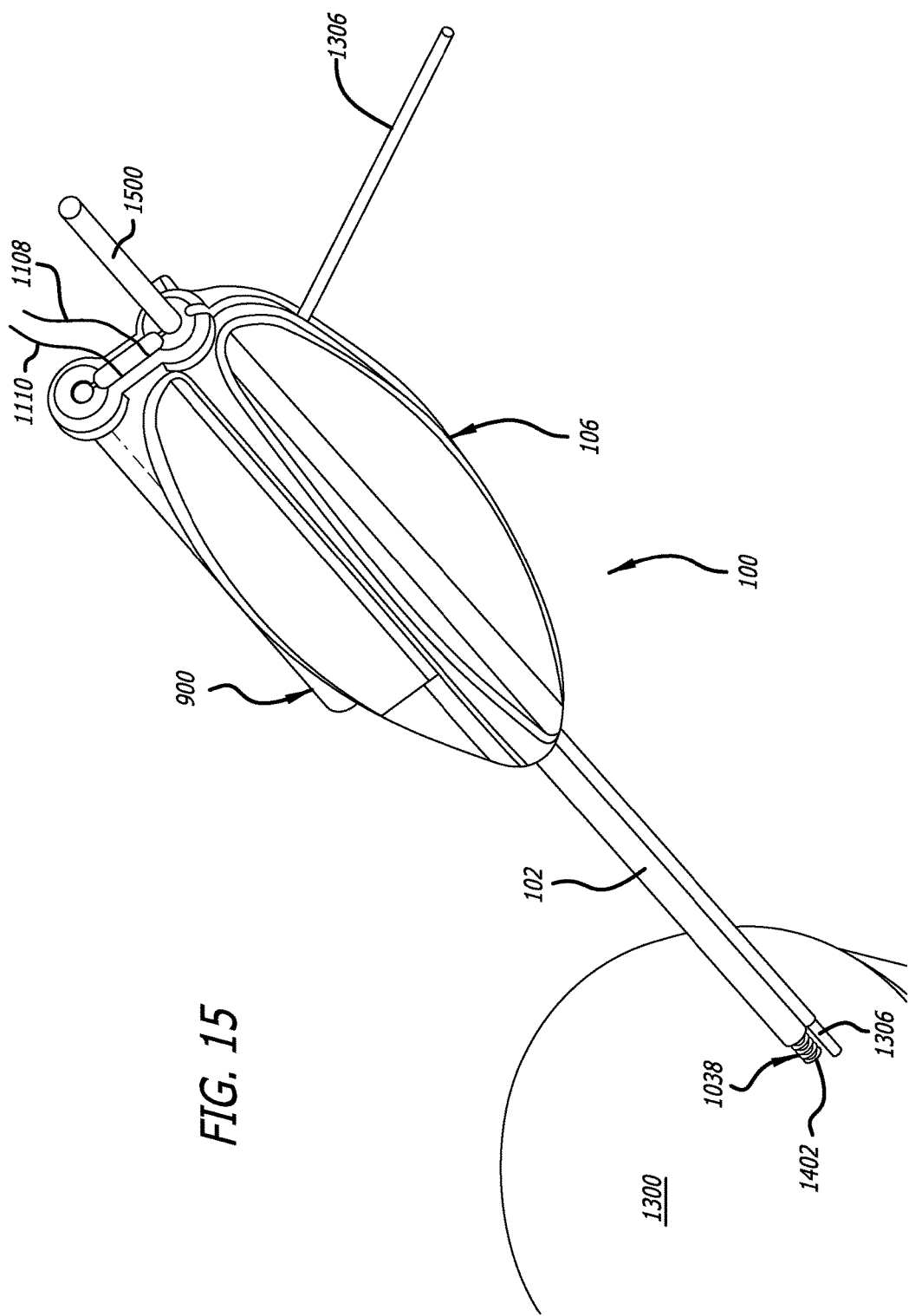
FIG. 15 shows a perspective view of the guide tool in relationship to the upper head of the humerus, in accordance with at least some embodiments.

FIG. 15 shows a perspective view of the guide tool in relationship to the upper head of the humerus, in accordance with at least some embodiments. In FIG. 15 the tissue 1304 is again omitted. Because the tissue 1304 is omitted, the distal end of the guide tool appears to hover above the bone, but in practice the distal end of the guide tool would abut the tissue 1304. In FIG. 15, the drill guide cartridge 700 (FIG. 14) has been removed, and the anchor cartridge 900 has been installed. More particularly, the anchor cartridge 900 is mated within the handle 106 of the guide tool 100 such that a delivery lumen defined by the tube 902 is coaxial with the delivery tube 102. In some example embodiments, installing the anchor cartridge 900 involves placing the anchor cartridge 900 such that the tube 902 is coaxial with the longitudinal central axis 112 (FIG. 1) of the delivery tube 102 (FIG. 1), and then telescoping the anchor cartridge 900 into the handle 106. The tack wire 1306 remains bent and in place during the removal of the drill guide cartridge 700 and installation of the anchor cartridge 900.

The bone anchor 1038 associated with the tube 902 is driven through a delivery tube 102 of the guide tool 100, through the tissue (not shown), and into the pilot hole 1402 within the bone. In example cases, the driving of the bone anchor 1038 into the pilot hole is by way of a delivery camp 1500. That is, the delivery camp 1500 is telescoped through the aperture 1100 of the anchor cartridge and through the tube 902 to abut a proximal end of the bone anchor 1038. The delivery camp 1500 is then used to push the bone anchor 1038 into and through the delivery tube 102 and into the pilot hole 1402. A small mallet (not shown) may be used to tamp the bone anchor along the delivery tube 102 and into the pilot hole 1402. FIG. 15, as an example, shows the bone anchor 1038 partially telescoped into the pilot hole 1402, but in practice the bone anchor 1038 is telescoped fully within the pilot hole 1402. As the bone anchor is pushed through the delivery tube 102, the suture line 1040 (not visible in FIG. 15) is likewise pulled along and at least partially removed from the suture volume 1032 (FIG. 10) of the anchor cartridge 900. After the bone anchor 1038 is within the pilot hole 1402, the delivery camp 1500 is removed or withdrawn from the guide tool 100 and the anchor cartridge 900.

With bone anchor 1038 in place, the next step in the example method may be to relocate or move the guide tool 100 to a second location. In particular, the movement of the guide tool 100 to the second location may involve removing the tack wire 1306 from the bone and guide tool 100, such as by pulling the tack wire 1306. Once the tack wire 1306 is fully removed, the suture line 1040 is dislodged or removed from the guide tool 100 through the slot 116 (FIG. 1) in the delivery tube 102, and dislodged or removed from the channel 140 (FIG. 3) of the channel region 132 (FIG. 1). That is, while the bone anchor 1038 remains in place, the loop 1200 (FIG. 12) and tightening line 1108 (FIG. 12) of suture line 1040 are removed from the guide tool 100, but remain connected to the loop 1202 (FIG. 2) and tightening line 1110 of suture line 1044.

Figure 16:
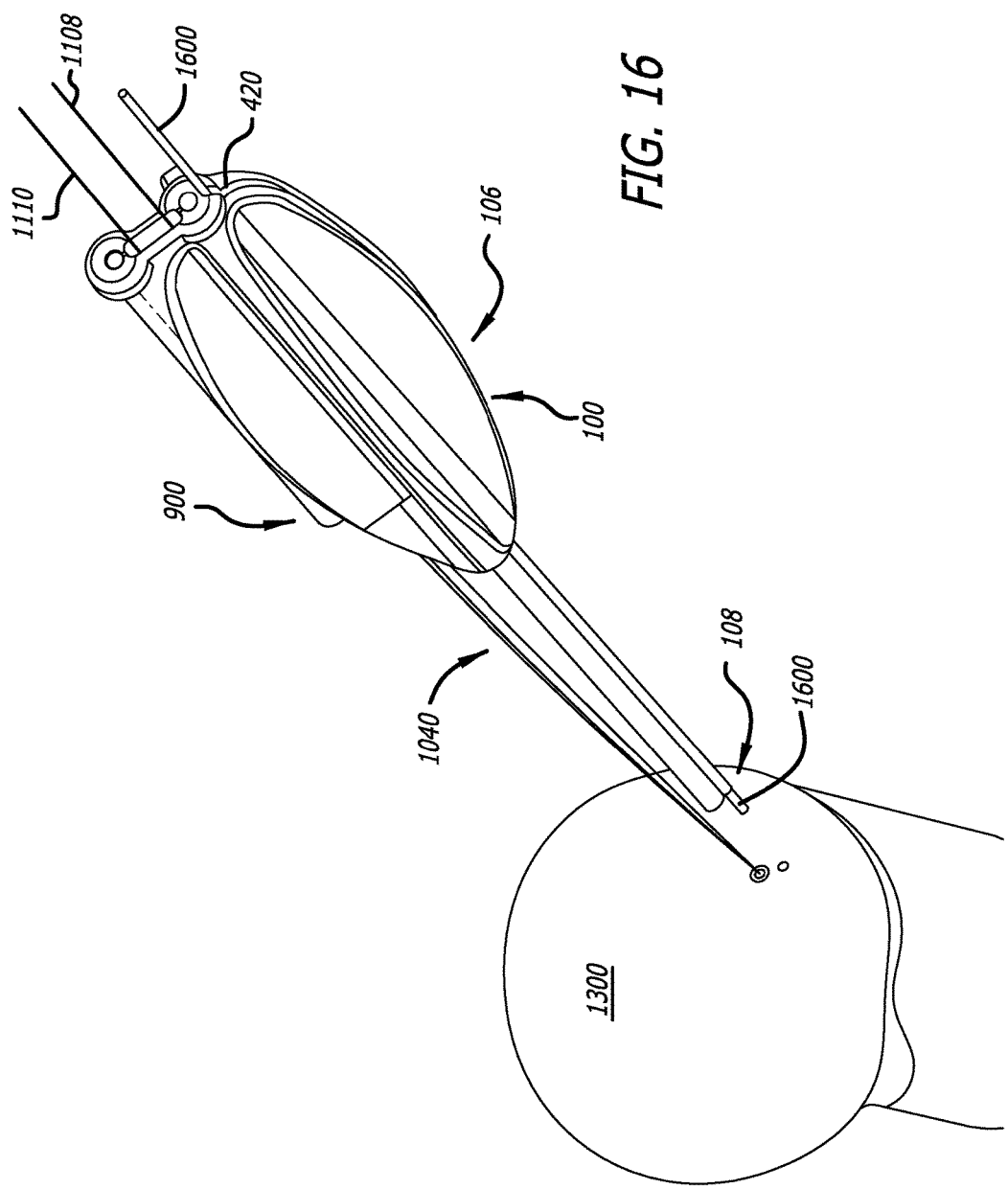
FIG. 16 shows a perspective view of the guide tool in relationship to the upper head of the humerus at a second location, in accordance with at least some embodiments.

FIG. 16 shows a perspective view of the guide tool in relationship to the upper head of the humerus at a second location, in accordance with at least some embodiments. The tissue is omitted from FIG. 16 so as not to further complicate the figure. The example method thus proceeds to abutting the distal end 108 of the guide tool 100 against the tissue at the second location displaced from the first location. Notice the suture line 1040, associated with the bone anchor previously installed, extending from the handle 106 to the bone anchor at the first location. With the distal end 108 abutting the tissue at the second location, a tack wire 1600 is telescoped through the guide tube 104 of the guide tool 100. In many cases the tack wire 1600 is new and/or distinct from the tack wire 1306 (FIG. 13) used at the first location. In particular, with the anchor cartridge 900 in the same orientation as when the first bone anchor 1038 (FIG. 15) was installed, the tack wire 1600 is telescoped through the notch 1054 of the anchor cartridge 900, along the trough 1050 (not visible) of the anchor cartridge 900, through the guide tube 104, and abutted against the tissue 1304. The tack wire 1600 is then rotated to cut or drill through the tissue 1304, and then cut or drill into the underlying bone. Once the distal end of the tack wire 1306 is within the bone, the proximal end of the tack wire 1306 is bent into the slot 420 within the handle 106 (the bent tack wire 1600 not specifically shown in FIG. 16). As before, the tack wire 1600 helps hold the distal end 108 of the guide tool 100 in place during the second bone anchor placement.

Figure 17:
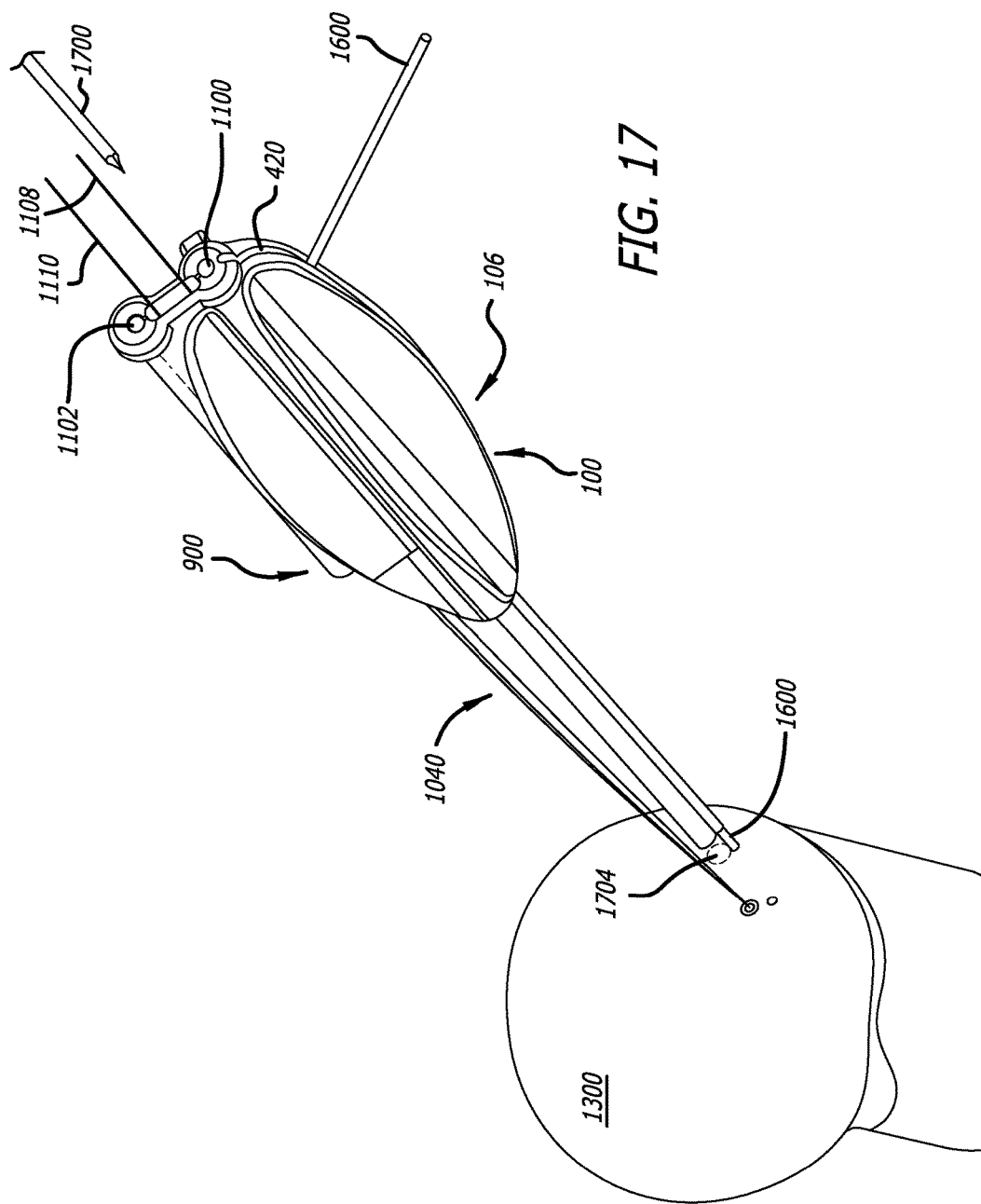
FIG. 17 shows a perspective view of the guide tool in relationship to the upper head of the humerus at the second location, in accordance with at least some embodiments.

FIG. 17 shows a perspective view of the guide tool in relationship to the upper head of the humerus at the second location, in accordance with at least some embodiments. As before, the tissue is omitted for purposes of discussion. FIG. 17 shows the proximal end of the tack wire 1600 bent into the slot 420 within the handle 106. Moreover, with the tissue omitted the distal end of the tack wire 1600 extending into the bone is visible. The tack wire 1600 extending into the bone holds the guide tool 100 in place around an axis defined by the tack wire 1600, and with the tack wire 1600 bent into the slot 420 the tack wire 1600 also holds the guide tool against rotation about the tack wire 1600.

Further visible in FIG. 17 is a drill wire 1700. The drill wire 1700 in example embodiments is metallic and has a diameter of 2.0 mm. In some cases, the drill wire 1700 has a spade or trocar tip (not specifically shown). In many cases the drill wire 1700 is new and/or distinct from the drill wire 1400 (FIG. 14) used at the first location. The drill wire 1700 has a length (not specifically delineated in the figure) that is longer than the sum of the length of the guide tool 100 and an expected depth of a pilot hole into which the bone anchor will be installed. The next step in the example method is telescoping the drill wire 1700 though the delivery tube 102 of the guide tool 100. In particular, the drill wire 1700 is telescoped through the aperture 1100 of the anchor cartridge 900, through the tube 902 (not visible), and through the delivery tube 102 to abut the tissue. Thus, the example tube 902 not only holds the bone anchor 1038 prior to installation at the first location, but also acts to guide the drill wire 1700 at the second location. The drill wire 1700 is then rotated to cut or drill through the tissue, and then cut or drill into the underlying bone. Thus, the distal end of the drill wire 1700 is used to create a second blind bore or second pilot hole in the bone. The example pilot hole 1704 is shown in dashed lines in FIG. 17. Thereafter, the drill wire 1700 is removed or withdrawn from the guide tool 100. The next step in the example method is removing the anchor cartridge 900 from the handle 106 of the guide tool 100. The anchor cartridge 900 is rotated, and then mated with the handle 106 of the guide tool 100 such that the second delivery lumen defined by the tube 910 is coaxial with the delivery tube 102. In some example embodiments, installing the anchor cartridge 900 involves placing the anchor cartridge 900 such that the tube 910 is coaxial with the longitudinal central axis 112 (FIG. 1) of the delivery tube 102, and then telescoping the anchor cartridge 900 into the handle 106.

Figure 18:
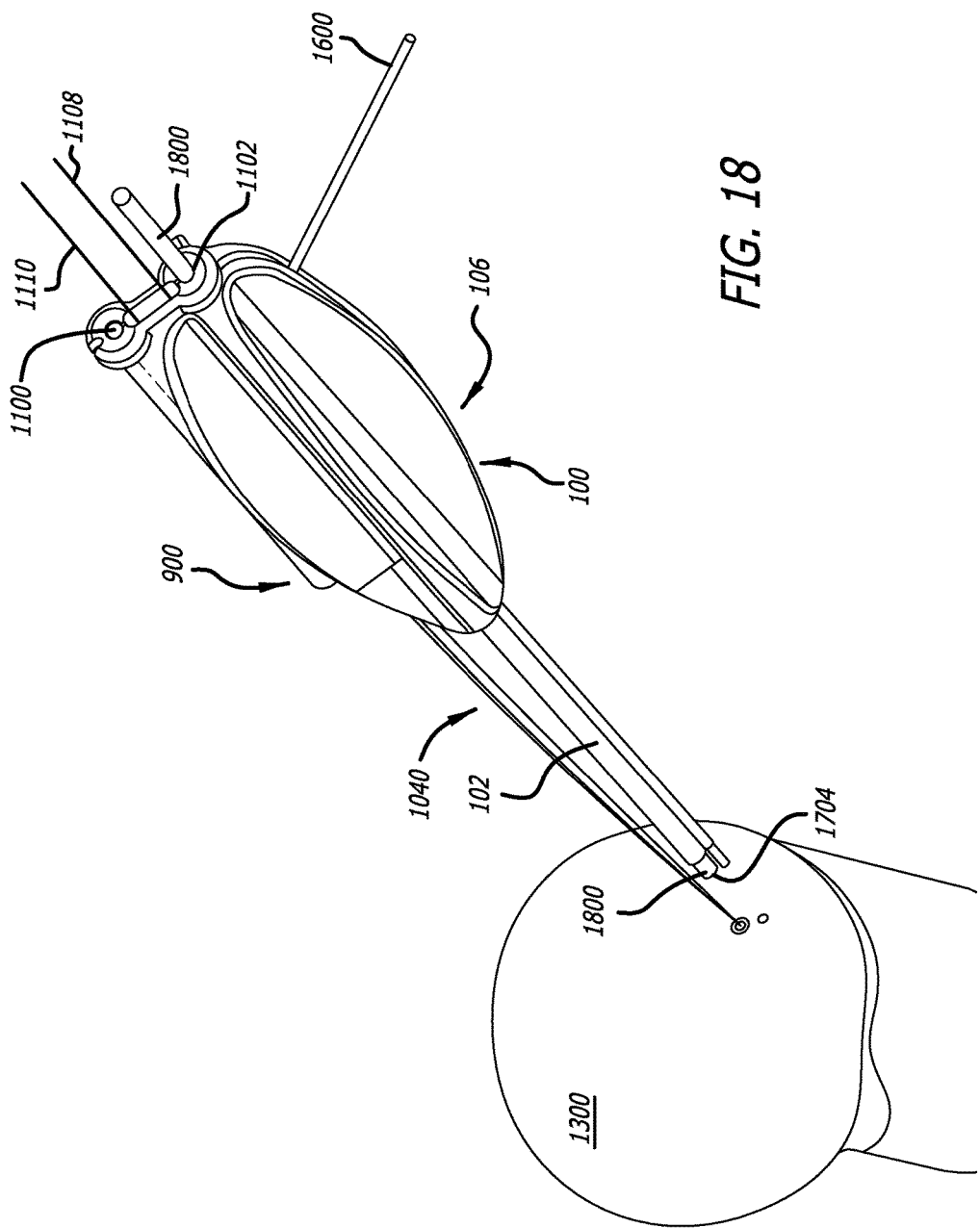
FIG. 18 shows a perspective view of the guide tool in relationship to the upper head of the humerus at the second position, in accordance with at least some embodiments.

FIG. 18 shows a perspective view of the guide tool in relationship to the upper head of the humerus, in accordance with at least some embodiments. In FIG. 18 the tissue is omitted again for purposes of discussion. In FIG. 18 the anchor cartridge 900 has been mated such that the tube 910 (not visible) is coaxial with the delivery tube 102. The tack wire 1600 remains bent and in place during the removal of and mating of the anchor cartridge 900. In accordance with example embodiments, the bone anchor 1042 associated with the tube 910 is driven through the delivery tube 102 of the guide tool 100, through the tissue (not shown), and into the bone by way of the pilot hole 1704. In example cases, the driving of the bone anchor 1042 into the pilot hole is by way of a delivery camp 1800. That is, the delivery camp 1800 is telescoped through the aperture 1102 of the anchor cartridge 900 and through the tube 910 to abut a proximal end of the bone anchor 1042. The delivery camp 1800 is then used to push the bone anchor 1042 through the delivery tube 102 and into the pilot hole 1704. A small mallet (not shown) may be used to tamp the bone anchor along the delivery tube 102 and into the pilot hole. As the bone anchor 1042 is pushed through the delivery tube 102, the suture line 1044 (not visible in FIG. 18) is likewise pulled along and at least partially removed from the suture volume 1032 (FIG. 10) of the anchor cartridge 900. After the bone anchor 1042 is within the pilot hole 1402, the delivery camp 1800 may be removed or withdrawn from the guide tool 100 and the anchor cartridge 900.

With example bone anchor 1042 in place, the next step in the example method may be to move the guide tool 100 away from the tissue and/or from the surgical site. In particular, the removal of the guide tool 100 may involve removing the tack wire 1600 from the bone and guide tool 100, such as by pulling the tack wire 1600. Once the tack wire 1600 is fully removed, the suture line 1044 is dislodged or removed from the guide tool 100 through the slot 116

(FIG. 1) in the delivery tube 102, and dislodged or removed from the channel 140 (FIG. 3) of the channel region 132 (FIG. 1). That is, while the bone anchor 1042 remains in place, the loop 1202 (FIG. 12) and tightening line 1110 (FIG. 12) of suture line 1044 are removed from the guide tool 100, but remain connected to the loop 1200 (FIG. 2) and tightening line 1108 of suture line 1040.

Figure 19:
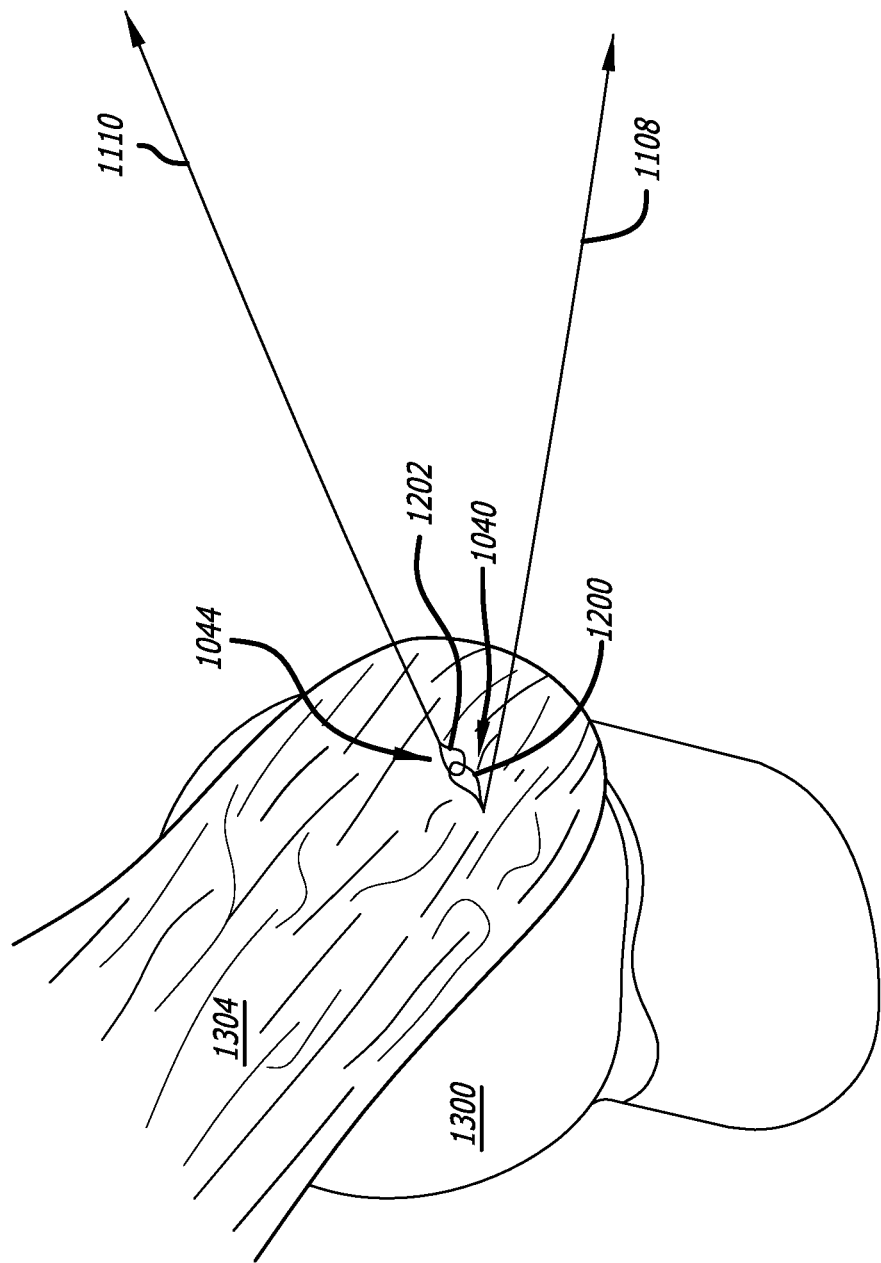
FIG. 19 shows a perspective view of the upper head of the humerus after removal of the guide tool, in accordance with at least some embodiments.

FIG. 19 shows a perspective view of the upper head of the humerus after removal of the guide tool, in accordance with at least some embodiments. In particular, visible in FIG. 19 is the tissue over the upper head of the 1300 of the humerus 1302. The guide tool 100 (FIG. 1) has been removed after installation of the two bone anchors, or at least moved to the side of surgical field. What remains are the suture line 1040 in the form of loop 1200 and tightening line 1108, as well as the suture line 1044 in the form of loop 1202 and tightening line 1110. To finalize the suture, the surgeon pulls on the tightening lines 1108 and 1110, which causes the slipknots (not visible) to slip and thus reduces the size of the loops 1200 and 1202. The loops 1200 and 1202 are thus pulled tight across tissue 1304, holding the tissue 1304 in place, and promoting reattachment in some cases.

The various example embodiments discussed to this point are for a single set of bone anchors creating a single suture. The repair using only two bone anchors with the suture created between them may be referred to as a "single row" repair. However, by using additional anchor cartridges 900 and corresponding additional sets of tack wires and drill wires, any number of sutures may be created in any suitable fashion. For example, a second suture may be created at a location offset from the first suture to form a "double-row" repair. The second suture in the double-row repair may be parallel to the first suture, or the second suture may cross the first suture to form an "X" pattern. In some cases, the second suture may cross the first suture such that the two sutures are perpendicular to each other. Further still, the various embodiments discussed to this point have assumed the suture to reside fully over the tissue. However, in other embodiments one bone anchor may be placed into the bone but not through the tissue, and in those cases the suture created may span the distal end of the tissue.

The Anchor Cartridge with Four Bone Anchors

Figure 20:
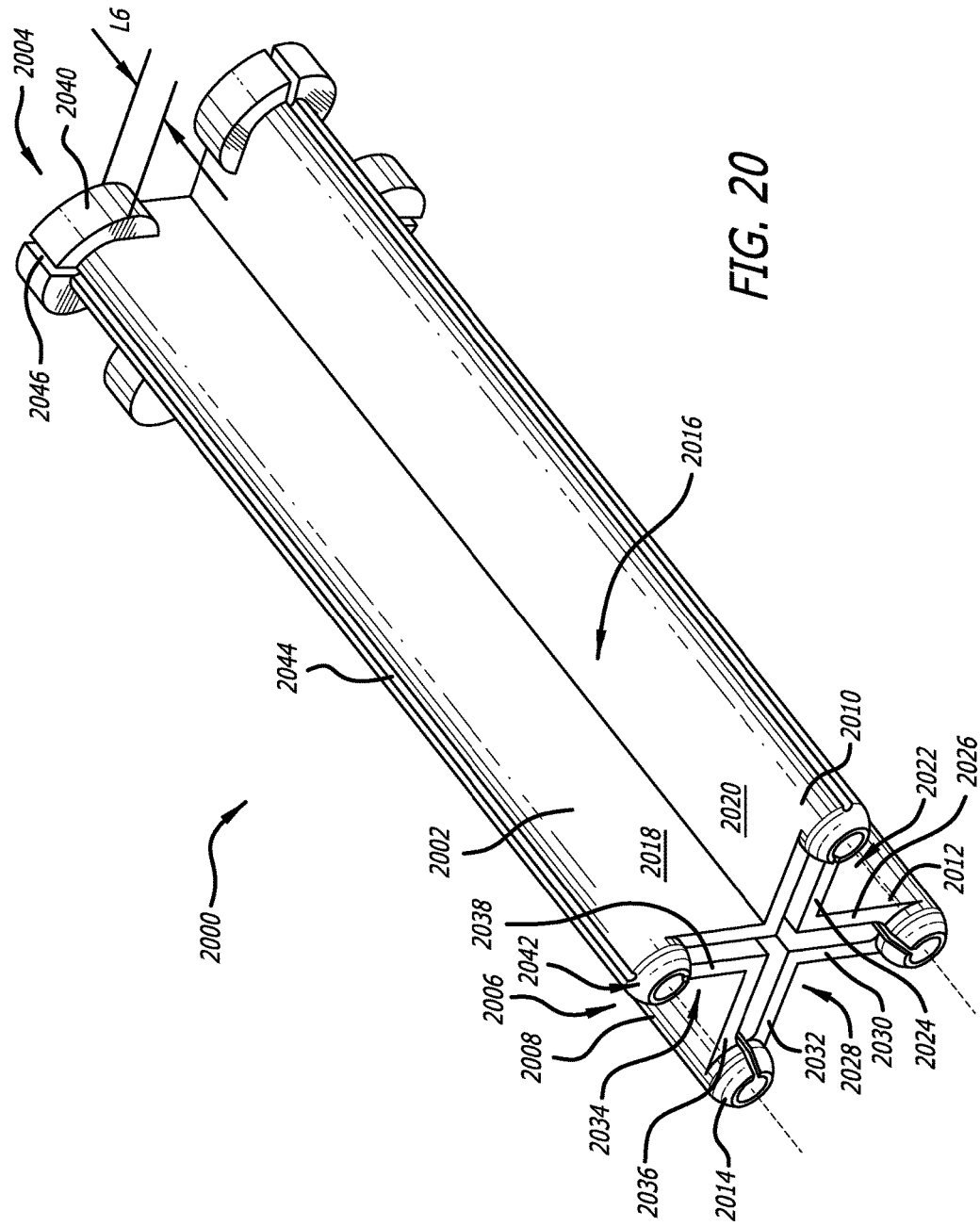
FIG. 20 shows a perspective view of an anchor cartridge having four bone anchors, and in accordance with at least some embodiments.

In accordance with further example embodiments, a double-row repair may be performed using a single anchor cartridge having four bone anchors. FIG. 20 shows a perspective view of an anchor cartridge 2000 having four bone anchors, and in accordance with at least some embodiments. In particular, the example anchor cartridge 2000 defines a tube 2002 defining a proximal end 2004, a distal end 2006, and a central axis 2008. Working clockwise, the example anchor cartridge 2000 further includes additional tubes 2010, 2012, and 2014. Each additional tube 2010, 2012, and 2014 has a proximal end and a distal end corresponding to tube 2002, but the proximal and distal ends of each additional tube 2010, 2012, and 2014 are not specifically marked so as not to further complicate the figure. Moreover, each additional tube 2010, 2012, and 2014 has a central axis that is parallel to the central axis 2008, but the additional central axes are not specifically marked so as not to further complicate the figure.

The example anchor cartridge 2000 further includes a plurality of side walls or spacers that hold the tubes in the respective orientations. Spacer 2016 couples to tube 2002 and tube 2010. The example spacer 2016 has a wall member 2018 coupled directly to the tube 2002, and the example spacer 2016 has a wall member 2020 coupled directly to the tube 2010. The wall members 2018 and wall member 2020 couple to each other on their ends opposite the tubes. The wall member 2018 in the example case is perpendicular to the wall member 2020, but other arrangements are possible, including a single wall member that forms an arch between the tube 2002 and the tube 2010. Spacer 2022 couples to tube 2010 and tube 2012. The example spacer 2022 has a wall member 2024 coupled directly to the tube 2010, and the example spacer 2022 has a wall member 2026 coupled directly to the tube 2012. The wall members 2025 and wall member 2026 couple to each other on their ends opposite the tubes. The wall member 2024 in the example case is perpendicular to the wall member 2026, but other arrangements are possible, including a single wall member that forms an arch between the tube 2010 and the tube 2012. Spacer 2028 couples to tube 2012 and tube 2014. The example spacer 2028 has a wall member 2030 coupled directly to the tube 2012, and the example spacer 2028 has a wall member 2032 coupled directly to the tube 2014. The wall members 2030 and wall member 2032 couple to each other on their ends opposite the tubes. The wall member 2030 in the example case is perpendicular to the wall member 2032, but other arrangements are possible, including a single wall member that forms an arch between the tube 2012 and the tube 2014. Spacer 2034 couples to tube 2014 and tube 2002. The example spacer 2034 has a wall member 2036 coupled directly to the tube 2014, and the example spacer 2034 has a wall member 2038 coupled directly to the tube 2002. The wall members 2036 and wall member 2038 couple to each other on their ends opposite the tubes. The wall member 2036 in the example case is perpendicular to the wall member 2038, but other arrangements are possible, including a single wall member that forms an arch between the tube 2014 and the tube 2002.

In the example anchor cartridge 2000, the wall member 2018 and wall member 2026 reside in the same plane. The wall member 2020 and the wall member 2036 reside in the same plane. The wall member 2024 and the wall member 2032 reside in the same plane, and the plane is parallel to the plane defined by wall member 2020 and wall member 2036. Wall member 2030 and wall member 2038 reside in the same plane, and the plane is parallel to the plane defined by wall member 2018 and wall member 2026.

The example anchor cartridge 2000 further defines a projection or flange 2040 disposed at the proximal end 2004 of the tube 2002. The flange 2040 extends outward from the anchor cartridge 2000. The example flange 2040 is shown as a partial right circular cylinder having a length L6 (measured parallel to the central axis 2008). In accordance with example embodiments, the length L6 is about the same as length L4 (FIG. 9) and for the same reasons. The example flange 2040 is selected, designed, and/or constructed to fit within the counter bore 500 (FIG. 5) at the proximal end 124 of the guide tool 100. The flange 2040 and the counter bore 500 thus act to lock or hold the proximal end 2004 of the anchor cartridge 2000 in the receptacle of the guide tool 100 when tube 2002 of the anchor cartridge 2000 is installed within the receptacle 134 of the handle 106.

Tube 2010 likewise defines a flange of similar design and having the same function when the tube 2010 is installed within the receptacle 134 (FIG. 1) of the handle 106. Tube 2012 likewise defines a flange of similar design and having the same function when the tube 2012 is installed within the receptacle of the handle 106. Tube 2014 likewise defines a flange of similar design and having the same function when the tube 2014 is installed within the receptacle of the handle 106. The flanges for the remaining tubes are not specifically numbered so as not to further complicate the figure. It follows that in use the example anchor cartridge 2000 is installed into the receptacle 134 in one of four orientations: one orientation with the tube 2002 within the channel 412 (FIG. 4) that defines the receptacle 134, and the tube 2002 coaxial with the delivery tube 102 (FIG. 1); a second orientation with the tube 2010 within the channel 412 that defines the receptacle 134, and the tube 2010 coaxial with the delivery tube 102; a third orientation with the tube 2012 within the channel 412 that defines the receptacle 134, and the tube 2012 coaxial with the delivery tube 102; and a fourth orientation with the tube 2014 within the channel 412 that defines the receptacle 134, and the tube 2010 coaxial with the delivery tube 102. An example surgical method where the anchor cartridge 2000 is installed in all four orientations is discussed more below.

Still referring to FIG. 20, the example anchor cartridge 2000 further defines a projection 2042 at distal end 2006 of the tube 2002. The projection 2042 extends beyond a distal end of the spacers 2016, 2022, 2028, and 2034. Each of the additional tubes 2010, 2012, and 2014 have a corresponding projection, the corresponding projections not specifically numbered so as not to further complicate the figure. In the example shown in FIG. 20, the projections are bulbous or hemispherical. However, the projections may take any suitable form, such as conical or conic frustums.

Still referring to FIG. 20, the example anchor cartridge 2000, and specifically the tube 2002, further defines a trough 2044 with an open top and a closed bottom. The trough 2044 opening outward at a radial direction or radial location opposite the slot (discussed more below) of the tube 2002. The trough 2044 runs from the proximal end 2004 of the tube 2002 to the distal end 2006 parallel to the central axis 2008. Moreover, the example flange 2040 has corresponding notch 2046 with an open top and a closed bottom. The closed bottom of the trough 2044 defines a radius of curvature with a center. When the anchor cartridge 2000 is installed within the receptacle 134 (FIG. 1) of the handle 106 (FIG. 1), the center of the radius of curvature resides on the longitudinal central axis 118 (FIG. 1) of the guide tube 104 (FIG. 1, and see also FIG. 4). The trough 2044 is aligned with the notch 2046. The trough 2044 and notch 2046 form a channel through which a tack wire is telescoped, as discussed above with respect to the example anchor cartridge 900.

In some example cases of anchor cartridge 2000, three of the four tubes will include corresponding troughs and notches, as in use three of the four tubes are used both for delivery of a bone anchor and as a drill guide for creation of the pilot hole for a bone anchor at another location. In other words, the anchor cartridge 2000 acts as a drill guide for creating the second and subsequent pilot holes. The fourth tube does not have the corresponding trough and notch as the fourth tube will not be used as a drill guide. However, so as not to dictate to the surgeon the order of use of the tubes or rotation direction of the anchor cartridge 2000 during use, in other cases all four tubes have a corresponding trough and all four flanges have a corresponding notch. In the example case of FIG. 20, tubes 2010 and 2012 have the corresponding trough, and their flanges have the corresponding notch, but those troughs and notches are not specifically numbered so as not to unduly complicate the figure.

Figure 21:
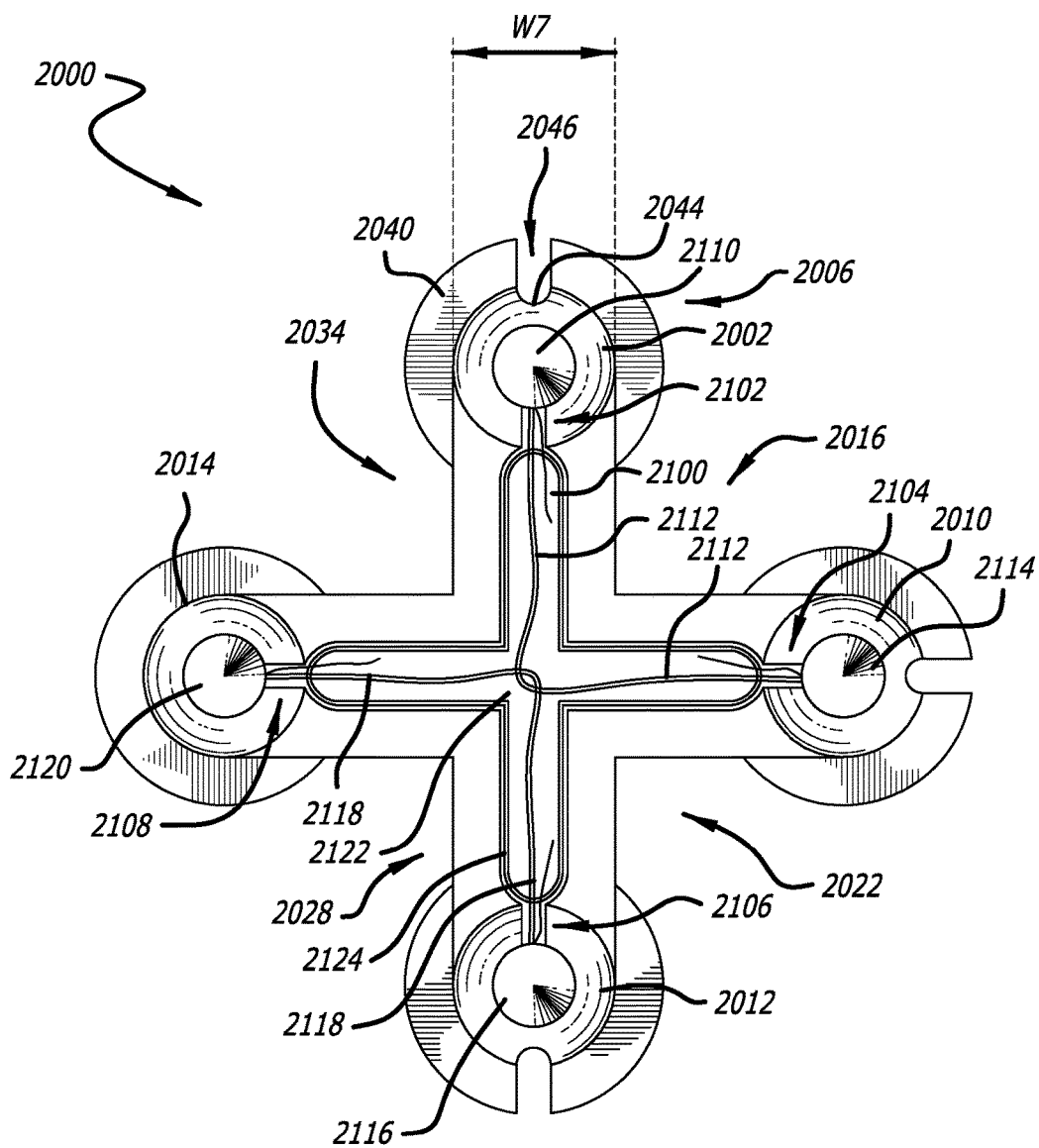
FIG. 21 shows an end-elevation view of the distal end of the anchor cartridge having four bone anchors, in accordance with at least some embodiments.

FIG. 21 shows an end-elevation view of the anchor cartridge 2000, looking from the distal end toward the proximal end. In particular, visible in FIG. 21 are the tube 2002, the tube 2010, tube 2012, and the tube 2014. Also visible in FIG. 21 are the spacer 2016, the spacer 2022, the spacer 2028, and the spacer 2034 separating the tubes 2002, 2010, 2012, and 2014. The flange 2040 associated with the tube 2002 is visible, along the remaining flanges (not specifically numbered) for the remaining tubes. The spacers 2016, 2022, 2028, and 2034 define a suture volume 2100 between them.

In accordance example embodiments, the tube 2002 defines a slot 2102 open to and extending from the distal end 2006 to the proximal end 2004 (not visible in FIG. 21). The slot 2102 creates a fluid communication channel between an inside diameter of the tube 2002 and the suture volume 2100. Similarly, the tube 2010 defines a slot 2104, tube 2012 defines a slot 2106, and tube 2014 defines a slot 2108. All the slots 2104, 2106, and 2108 extend from the distal ends to the proximal ends (not visible in FIG. 21) of their respective tubes. Each slots 2104, 2016, and 2108 thus creates a fluid communication channel between an inside diameter of its respective tube and the suture volume 2100.

Also visible in FIG. 21 are end views of four bone anchors. In particular, a bone anchor 2110 is disposed within the tube 2002. A suture line 2112 is associated with a proximal end (not visible) of the bone anchor 2110, and the suture line 1040 extends through the slot 2102 of the tube 2002 into the suture volume 2100. Similarly, a bone anchor 2114 is disposed within the tube 2010. The suture line 2112 is likewise associated with a proximal end (not visible) of the bone anchor 2114, and the suture line 2112 extends through the slot 2104 of the tube 2010 into the suture volume 2100. A bone anchor 2116 is disposed within the tube 2012. A suture line 2118 is associated with a proximal end (not visible) of the bone anchor 2116, and the suture line 2118 extends through the slot 2106 of the tube 2012 into the suture volume 2100. Similarly, a bone anchor 2120 is disposed within the tube 2012. The suture line 2118 is likewise associated with a proximal end (not visible) of the bone anchor 2120, and the suture line 2118 extends through the slot 2108 of the tube 2012 into the suture volume 2100. In accordance with at least some embodiments, the suture lines 2112 and 2118, after extending through the slots, are disposed within an internal volume 2122 of a suture sleeve 2124.

Still referring to FIG. 21, the example anchor cartridge 2000 defines a width W7 (measured perpendicular to the central axis 2008 (FIG. 20)). The width W7 is the same or substantially the same as the width W6 (FIG. 10) for the same reasons, and those reasons will not be repeated again here so as not to unduly lengthen the specification. Moreover, each arm of the anchor cartridge 2000, with each arm corresponding to a tube, has the same width measured the same way.

In the view of FIG. 21 also visible in association with tube 2002 is the trough 2044 with an open top and a closed bottom. The trough 2044 opening outward at a radial direction or radial location opposite the slot 2102 of the tube 2002. The flange 2040 has the corresponding notch 2046 with an open top and a closed bottom. The trough 2044 is aligned with the notch 2046. Again, tubes 2010, 2012, and 2014 have corresponding troughs, and their flanges have corresponding notches, but those features are not specifically numbered so as not to unduly complicate the figure. In yet still other cases, the spacing or offset between the delivery tube 102 (FIG. 1) and the guide tube 104 (FIG. 1) may be large enough that the trough can be omitted from the tubes, though the notches may be still be present.

The tubes 2002, 2010, 2012, and 2014, particularly their outer surfaces not "covered" or abutting by the spacers 2016, 2022, 2028, and 2034, each define semi-circular regions. Referring simultaneously to FIGS. 4 and 21, the bottom 408 of the channel 412 that at least partially defines the receptacle 134 is curved and has the radius of curvature 417. The semi-circular regions of the outer surfaces of the tubes 2002, 2010, 2012, and 2014 are thus a negative image of the bottom 408. However, other shapes are possible for the bottom 408 as discussed above, and the outer surfaces of the tubes 2002, 2010, 2012, and 2014 need only be able to fit within the bottom 408, as discussed with respect to the anchor cartridge 900.

Figure 22:
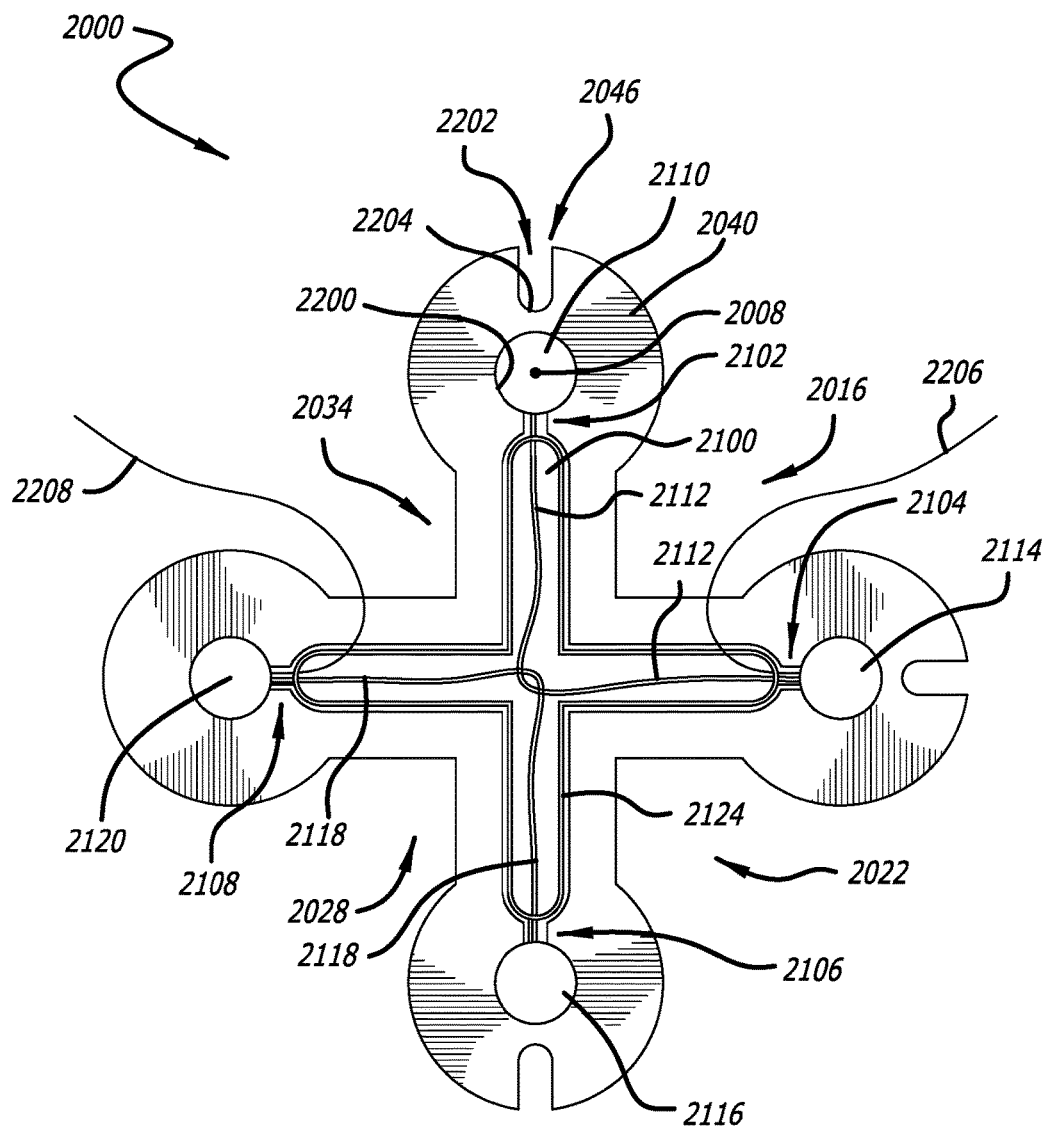
FIG. 22 shows an end-elevation view of the proximal end of the anchor cartridge having four bone anchors, in accordance with at least some embodiments.

FIG. 22 shows an end-elevation view of the proximal end of the anchor cartridge 2000, in accordance with at least some embodiments. In particular, visible in FIG. 22 is the flange 2040 at the top of the of the figure, and the remaining flanges spaced apart and forming four corners of the example anchor cartridge 2000. Between the two flanges are the spacers 2016, 2022, 2028, and 2034. Flange 2040 defines an aperture 2200 that is circular, and the central axis of the aperture 2200 is coaxial with the central axis 2008 of the tube 2002 (the central axis 2008 is perpendicular to the plane of the page, and thus shown as a dot). Each of the remaining flanges (not specifically numbered) define a corresponding aperture coaxial with the central axis of the respective tube. Further visible in FIG. 22 is the notch 2046 in the flange 2040. The notch 2046 defines an open top 2202 and a closed bottom 2204. The notch 2046 is shown to open outward at a radial location or radial direction opposite the location of the slot 2102. Two of the three remaining flanges have corresponding notches opening outward at radial locations or radial directions opposite the location of their respective slots.

Visible through the apertures are the bone anchors 2110, 2114, 2116, and 2120. Further visible in FIG. 22 is the fact the slots 2102, 2104, 2106, and 2108 are open on their respective proximal ends of the anchor cartridge 2000. Each slot provides fluid communication between the internal volume of its respective tube and the suture volume 2100 defined between the spacers 2016, 2022, 2028, and 2034. Further visible in FIG. 22 are the suture line 2112, the suture line 2118, and the suture sleeve 2124, all within the suture volume 2100. The suture line 2112 includes a bitter end or tightening line 2206, and the suture line 2118 include a bitter end or tightening line 2208. The use of tightening lines 2206 and 2208 is discussed more below in relation to tightening the suture over and against the tissue.

The example anchor cartridge 2000 includes only two tightening lines 2206 and 2208 as an example of a suture tying method and system where two bone anchors (e.g., bone anchors 2110 and 2114) share single loop of a slipknot, such that the surgeon need only pull one tightening end to affix the suture between the two bone anchors. Similarly, in the example system the other two bone anchors (e.g., bone anchors 2116 and 2120) share single loop of a slipknot, such that the surgeon need only pull one tightening end to affix the suture between the remaining two bone anchors. However, the suturing method and system discussed with respect to the anchor cartridge 900 may also be used with the anchor cartridge 2000, such that the surgeon separately pulls a tightening end associated with each bone anchor (e.g., each bone anchor having a slipknot and corresponding loop, and the loops coupled together for two bone anchors).

Referring briefly to FIG. 12, FIG. 12 shows the cross-sectional view of the example anchor cartridge 900. A cross-sectional view of the example anchor cartridge 2000 is omitted as such would be somewhat duplicative of the cross-sectional view of example anchor cartridge 900 as shown in FIG. 12. The considerations regarding the length L3 of the anchor cartridge 900 in relation to the length L5 of the bone anchors are equally applicable to the example anchor cartridge 2000. The distance between two tubes that would be seen in a cross-sectional view (e.g., tubes 2002 and 2012) would be greater for anchor cartridge 2000 than shown in FIG. 12 owing to the depth of the receptacle 134 (FIG. 1). If the walls that define the receptacle were made shorter, the distance between two tubes that would be seen in a cross-sectional view (e.g., tubes 2010 and 2014) could be made shorter.

Figure 23:
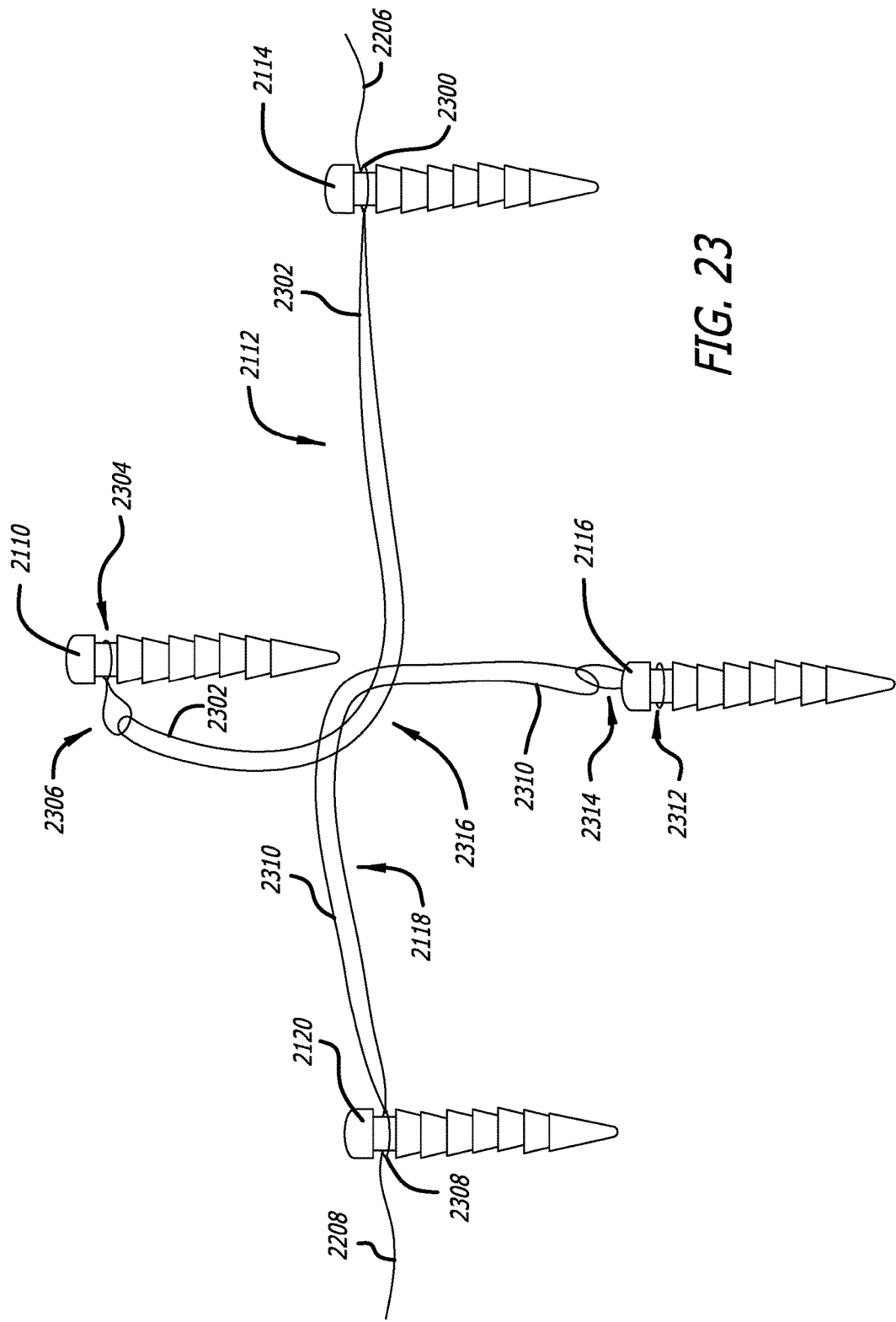
FIG. 23 shows a perspective view of four bone anchors and corresponding suture lines, in accordance with at least some embodiments.

FIG. 23 shows a perspective view of four bone anchors and corresponding suture lines, in accordance with at least some embodiments. In particular, FIG. 23 shows the four bone anchors 2110, 2114, 2116, and 2120. FIG. 23 also shows the suture line 2112 associated with the bone anchors 2110 and 2114, and the suture line 2118 associated with the bone anchors 2116 and 2120. Suture line 2112 comprises a slipknot 2300 tied to a bollard of the bone anchor 2114. The slipknot 2300 defines the tightening line 2206 as well as a loop 2302. In the example system, an eye splice 2304 defines an eyelet 2306 (e.g., a long bury splice), and the eye splice 2304 is associated with bone anchor 2110. In particular, the bitter end of the eye splice 2304 is tied to a bollard of the bone anchor 2110, and the loop 2302 extends through the eyelet 2306. Suture line 2118 comprises a slipknot 2308 tied to a bollard of the bone anchor 2120. The slipknot 2308 defines the tightening line 2208 as well as a loop 2310. In the example system, an eye splice 2312 defines an eyelet 2314 (e.g., a long bury splice), and the eye splice 2312 is associated with bone anchor 2116. In particular, the bitter end of the eye splice 2312 is tied to a bollard of the bone anchor 2116, and the loop 2310 extends through the eyelet 2314. In the example system, both legs of the loop 2302 extends around the both legs of the loop 2310 (at crossing 2316). When the example anchor cartridge 2000 (FIG. 20) is assembled but before use, the suture lines 2112 and 2118 extend through the slots associated with the tubes and into the suture volume 2100 (FIG. 21). The eyelets 2306 and 2314 may also at least partially extend into the suture volume 2100 depending on the length of the leads tied back to the respective bollards.

The association of slipknots and eye splices shown in FIG. 23 is merely an example, as the slipknots and thus the tightening ends may be associated with any two bone anchors and corresponding tubes. Once the bone anchors are installed, the surgeon pulls the tightening lines 2206 and 2208 to make the loops 2302 and 2310 smaller until the loop abuts the tissue, thus forming the overall suture. Of course, many suture line tying methods are possible. For each bone anchor could have its own slip knot, loop, and tightening end (e.g., the anchor cartridge 900), and thus four tightening ends would be present. Further still, the suture line tying method need not be uniform across the pairs, such that two bone anchors may have respective tightening lines, and the other two bone anchors may have a single tightening line.

Example Double-Row Repair Methods

The specification now turns to an example method of connecting tissue to bone utilizing the guide tool 100, the drill guide cartridge 700, and the anchor cartridge 2000 described above, all to implement a double-row repair. The example method that follows is based on the developmental context, but should not be construed as a limitation of the applicability of the various devices. As with single-row repairs, the reattachment of the tissue may take place arthroscopically, and thus additional instruments and systems may be present. The various devices and systems used to implement arthroscopic procedures are not shown so as not to unduly complicate the discussion.

The initial steps in preparing for placement of the first bone anchor in the double-row repair are the same as the initial steps for placement of the first bone anchor in the single-row repair. FIGS. 13 and 14 and the related discussion are thus equally applicable here, including use the drill guide cartridge 700 when placing the first tack wire and making the first pilot hole. After the first pilot hole is created, the drill wire is removed, and the drill guide cartridge 700 is removed. Thereafter, the anchor cartridge 2000 is installed.

Figure 24:
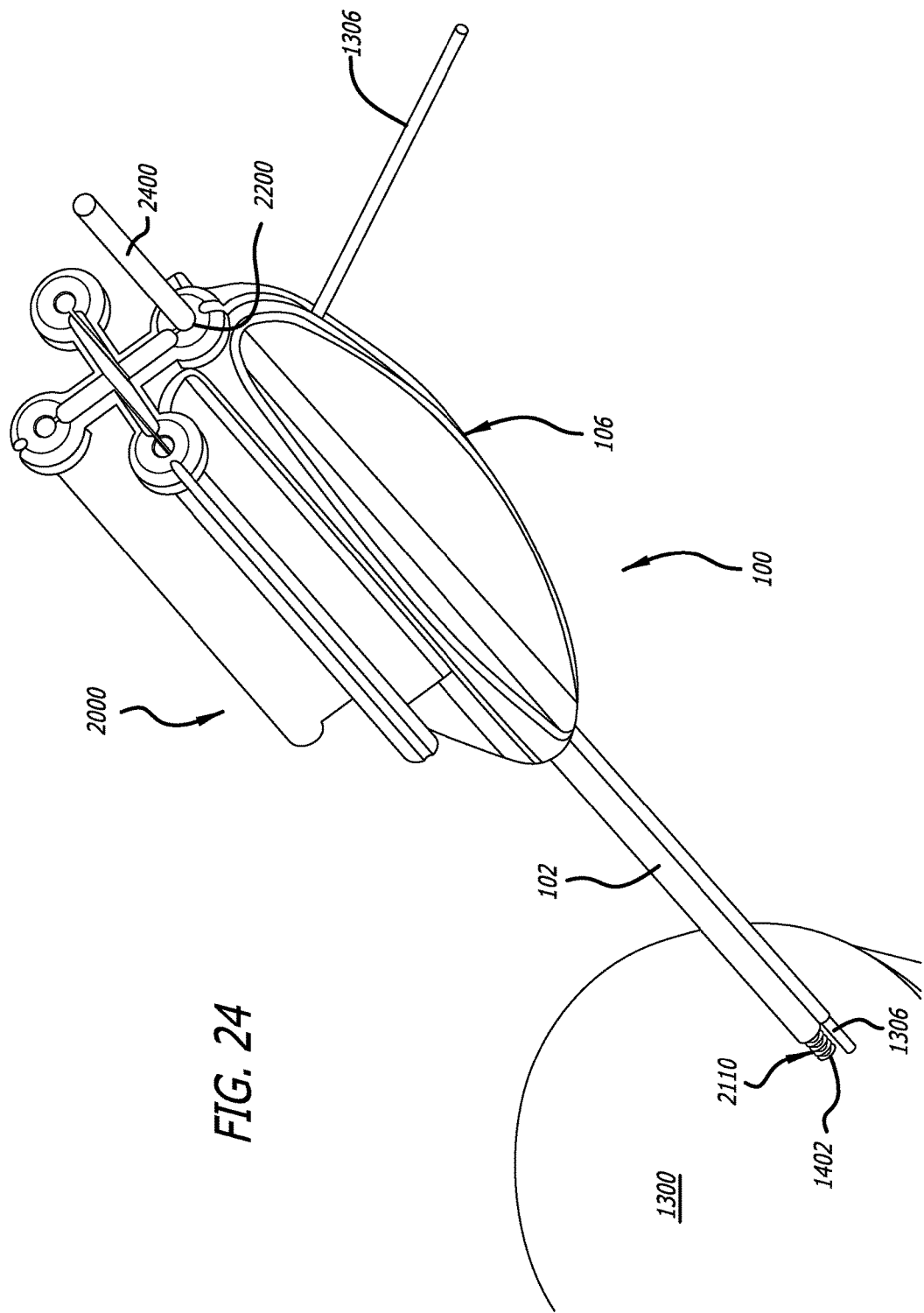
FIG. 24 shows a perspective view of the guide tool and anchor cartridge having four bone anchors in relationship to the upper head of the humerus for a double-row repair, in accordance with at least some embodiments.

FIG. 24 shows a perspective view of the guide tool in relationship to the upper head of the humerus, in accordance with at least some embodiments. In FIG. 24 the tissue 1304 is omitted for purposes of discussion. In FIG. 24, the drill guide cartridge 700 (FIG. 14) has been removed, and the anchor cartridge 2000 has been installed. More particularly, the anchor cartridge 2000 is mated within the handle 106 of the guide tool 100 such that a delivery lumen defined by the tube 2002 (not visible) is coaxial with the delivery tube 102. The tack wire 1306 remains bent and in place during the removal of the drill guide cartridge 700 and installation of the anchor cartridge 2000.

The bone anchor 2110 associated with the tube 2002 is driven through the delivery tube 102 of the guide tool 100, through the tissue (not shown), and into the pilot hole 1402 within the bone. In example cases, the driving of the bone anchor 2110 into the pilot hole is by way of a delivery camp 2400. That is, the delivery camp 2400 is telescoped through the aperture 2200 and through the tube 2002 (not visible) to abut a proximal end of the bone anchor 2110. The delivery camp 2400 is then used to push the bone anchor 2110 into and through the delivery tube 102 and into the pilot hole 1402. FIG. 24, as an example, shows the bone anchor 2110 partially telescoped into the pilot hole 1402, but in practice the bone anchor 2110 is telescoped fully within the pilot hole 1402. As the bone anchor 2110 is pushed through the delivery tube 102, the suture line 2112 (not visible in FIG. 24) is likewise pulled along and at least partially removed from the suture volume 2100 (FIG. 10) of the anchor cartridge 2000. After the bone anchor 2110 is within the pilot hole 1402, the delivery camp 1500 is removed or withdrawn from the guide tool 100 and the anchor cartridge 2000.

With bone anchor 2110 in place, the next step in the example method may be to relocate or move the guide tool 100 to a second location. In particular, the movement of the guide tool 100 to the second location may involve removing the tack wire 1306 from the bone and guide tool 100, such as by pulling the tack wire 1306. Once the tack wire 1306 is fully removed, the suture line 2112 is dislodged or removed from the guide tool 100 through the slot 116 (FIG. 1) in the delivery tube 102, and dislodged or removed from the channel 140 (FIG. 3) of the channel region 132 (FIG. 1). That is, while the bone anchor 2110 remains in place, the loop 2302 (FIG. 23) and tightening line 2206 (FIG. 23) of suture line 2112 are removed from the guide tool 100.

Figure 25:
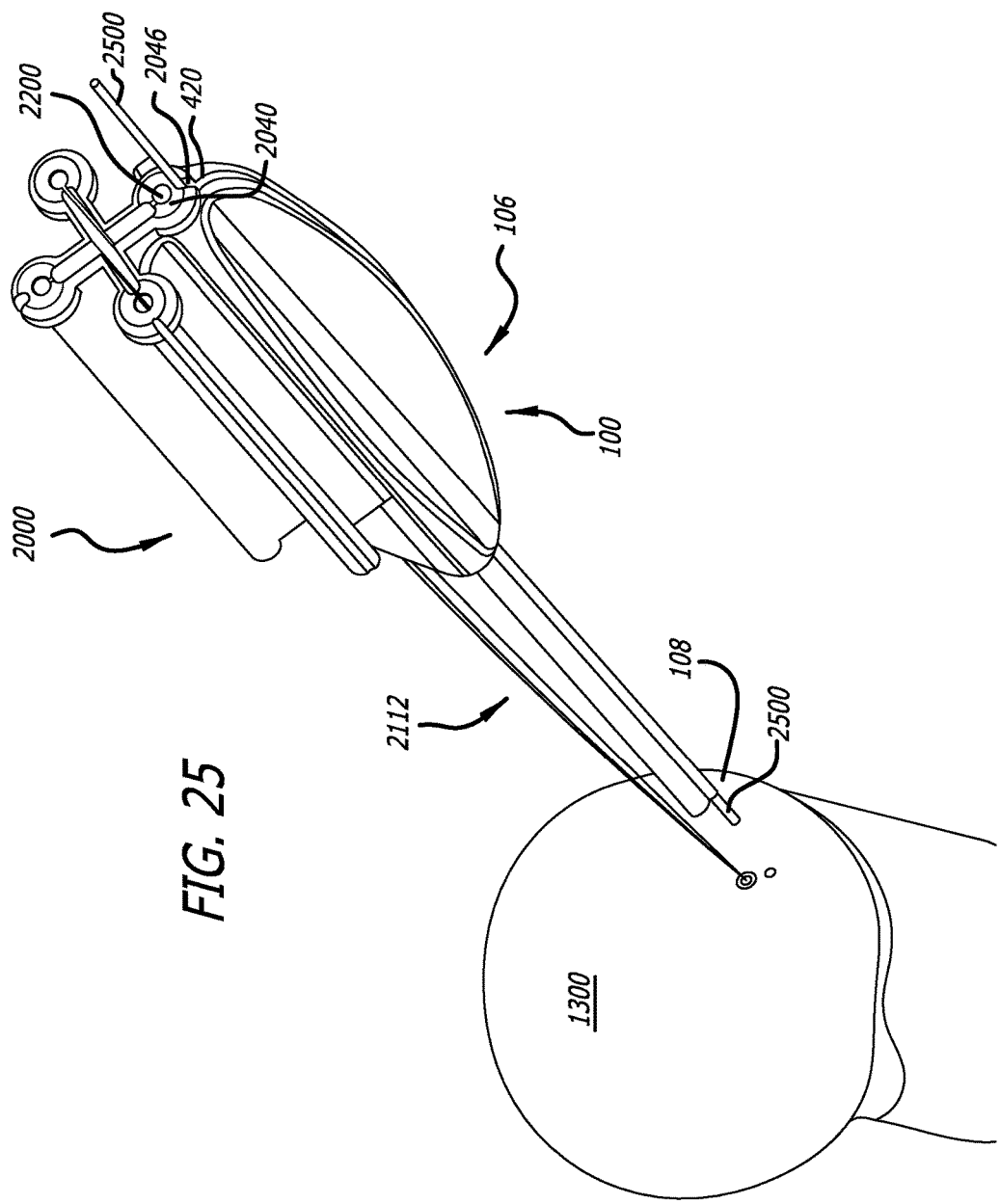
FIG. 25 shows a perspective view of the guide tool and anchor cartridge having four bone anchors in relationship to the upper head of the humerus at a second location for a double-row repair, in accordance with at least some embodiments.

FIG. 25 shows a perspective view of the guide tool in relationship to the upper head of the humerus at a second location, in accordance with at least some embodiments. The tissue is again omitted from FIG. 25. The example method thus proceeds to abutting the distal end 108 of the guide tool 100 against the tissue at the second location displaced from the first location. Notice the suture line 2112, associated with the bone anchor previously installed, extending from the handle 106 to the bone anchor at the first location. With the distal end 108 abutting the tissue at the second location, a tack wire 2500 is telescoped through the guide tube 104 of the guide tool 100. In particular, with the anchor cartridge 2000 in the same orientation as when the first bone anchor 2110 (FIG. 24) was installed, the tack wire 2500 is telescoped through the notch 2046 of the flange 2040 of the anchor cartridge 2000, along the trough 2044 (not visible) of the anchor cartridge 2000, through the guide tube 104, and abutted against the tissue 1304. The tack wire 2500 is then rotated to cut or drill through the tissue 1304, and then cut or drill into the underlying bone. Once the distal end of the tack wire 2500 is within the bone, the proximal end of the tack wire 2500 is bent into the slot 420 within the handle 106 (the bent tack wire 2500 not specifically shown in FIG. 25). As before, the tack wire 2500 helps hold the distal end 108 of the guide tool 100 in place during the second bone anchor placement.

Figure 26:
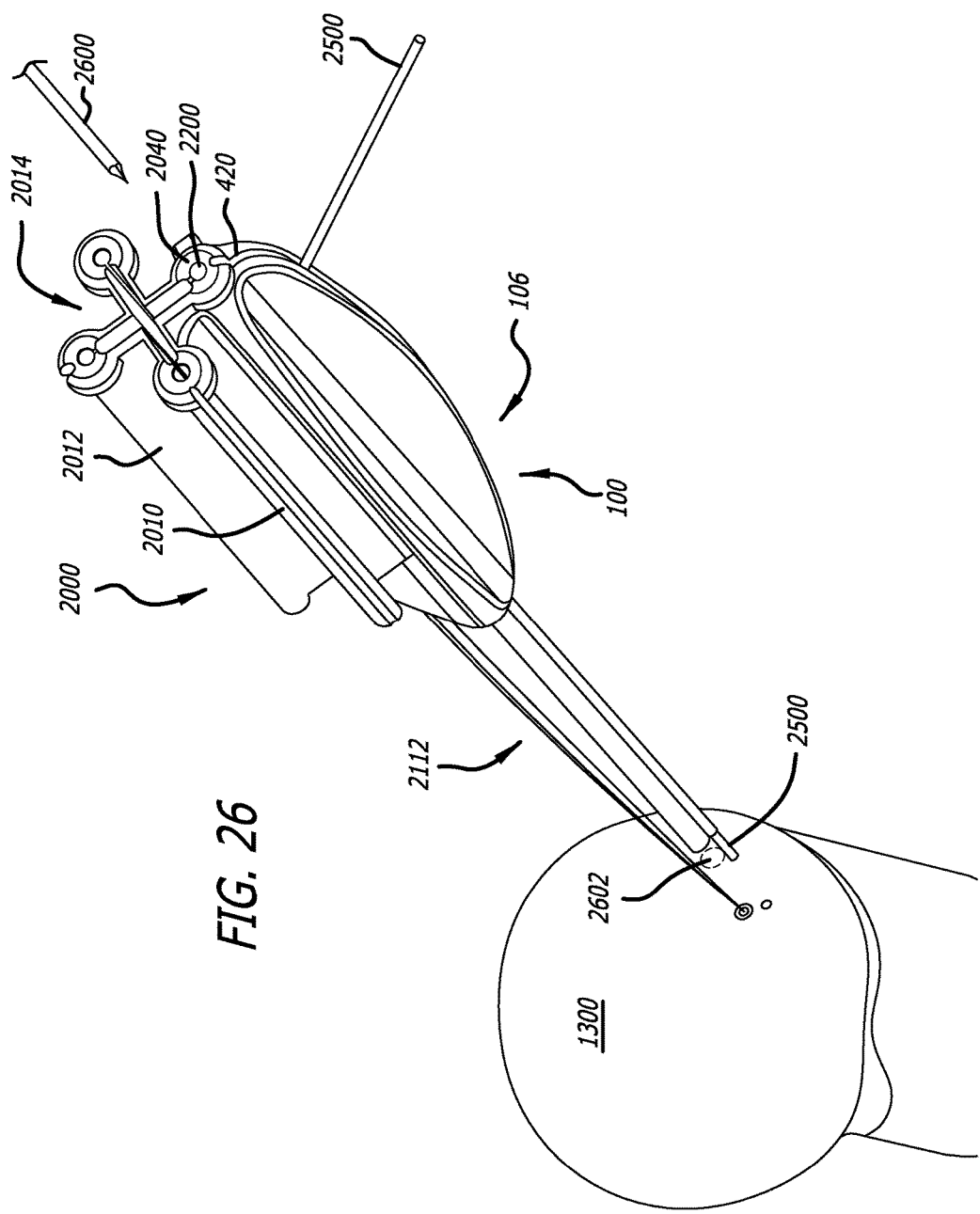
FIG. 26 shows a perspective view of the guide tool and anchor cartridge having four bone anchors in relationship to the upper head of the humerus at the second location for a double-row repair, in accordance with at least some embodiments.

FIG. 26 shows a perspective view of the guide tool in relationship to the upper head of the humerus at the second location, in accordance with at least some embodiments. As before, the tissue is omitted for purposes of discussion. FIG. 26 shows the proximal end of the tack wire 2500 bent into the slot 420 within the handle 106. Moreover, with the tissue omitted the distal end of the tack wire 2500 extending into the bone is visible. The tack wire 2500 extending into the bone holds the guide tool 100 in place around an axis defined by the tack wire 2500, and with the tack wire 2500 bent into the slot 420 the tack wire 2500 also holds the guide tool 100 against rotation about the tack wire 2500.

Further visible in FIG. 26 is a drill wire 2600. The next step in the example method is telescoping the drill wire 2600 though the tube 2002 (not visible) of the guide tool 100. In particular, the drill wire 2600 is telescoped through the aperture 2200 of the flange 2040 of the anchor cartridge 2000, through the tube 2002 (not visible), and through the delivery tube 102 to abut the tissue. Thus, the example tube 2002 not only holds the bone anchor 2110 prior to installation at the first location, but also acts to guide the drill wire 2600 at the second location. The drill wire 2600 is then rotated to cut or drill through the tissue, and then cut or drill into the underlying bone. Thus, the distal end of the drill wire 2600 is used to create a second blind bore or second pilot hole in the bone. The example pilot hole 2602 is shown in dashed lines in FIG. 26. Thereafter, the drill wire 2600 is removed or withdrawn from the guide tool 100. The next step in the example method is removing the anchor cartridge 2000 from the handle 106 of the guide tool 100. The anchor cartridge 2000 is rotated (in the view of FIG. 26, rotated counter clockwise), and then mated with the handle 106 of the guide tool 100 such that the delivery lumen defined by the tube 2010 is coaxial with the delivery tube 102. The bone anchor 2114 in the tube 2010 is then telescoped through the delivery tube 102 into the pilot hole 2602 by way of a delivery camp.

The guide tool 100 is then moved to a third location. A new tack wire is installed as previously discussed, and a pilot hole at the third location is drilled through the delivery tube 2010. Thereafter, the anchor cartridge 2000 is again rotated, this time such that the tube 2012 is coaxial with the delivery tube 102. Once the anchor cartridge 2000 is rotated, the bone anchor 2116 in the tube 2012 is then telescoped through the delivery tube 102 into the pilot hole by way of a delivery camp.

The guide tool 100 is then moved to a fourth location. A new tack wire is installed as previously discussed, and a pilot hole at the fourth location is drilled through the tube 2012. Thereafter, the anchor cartridge 2000 is again rotated, this time such that the tube 2014 (FIG. 20) is coaxial with the delivery tube 102. Once the anchor cartridge 2000 is rotated, the bone anchor 2120 in the tube 2014 is then telescoped through the delivery tube 102 into the pilot hole by way of a delivery camp. Inasmuch as the bone anchor 2120 is the final bone anchor in the double-row repair, the tube 2014 is not needed as a drill guide for a subsequent pilot hole, and thus the flange associated with the tube 2014 need not have a notch similar to the other flanges.

Figure 27:
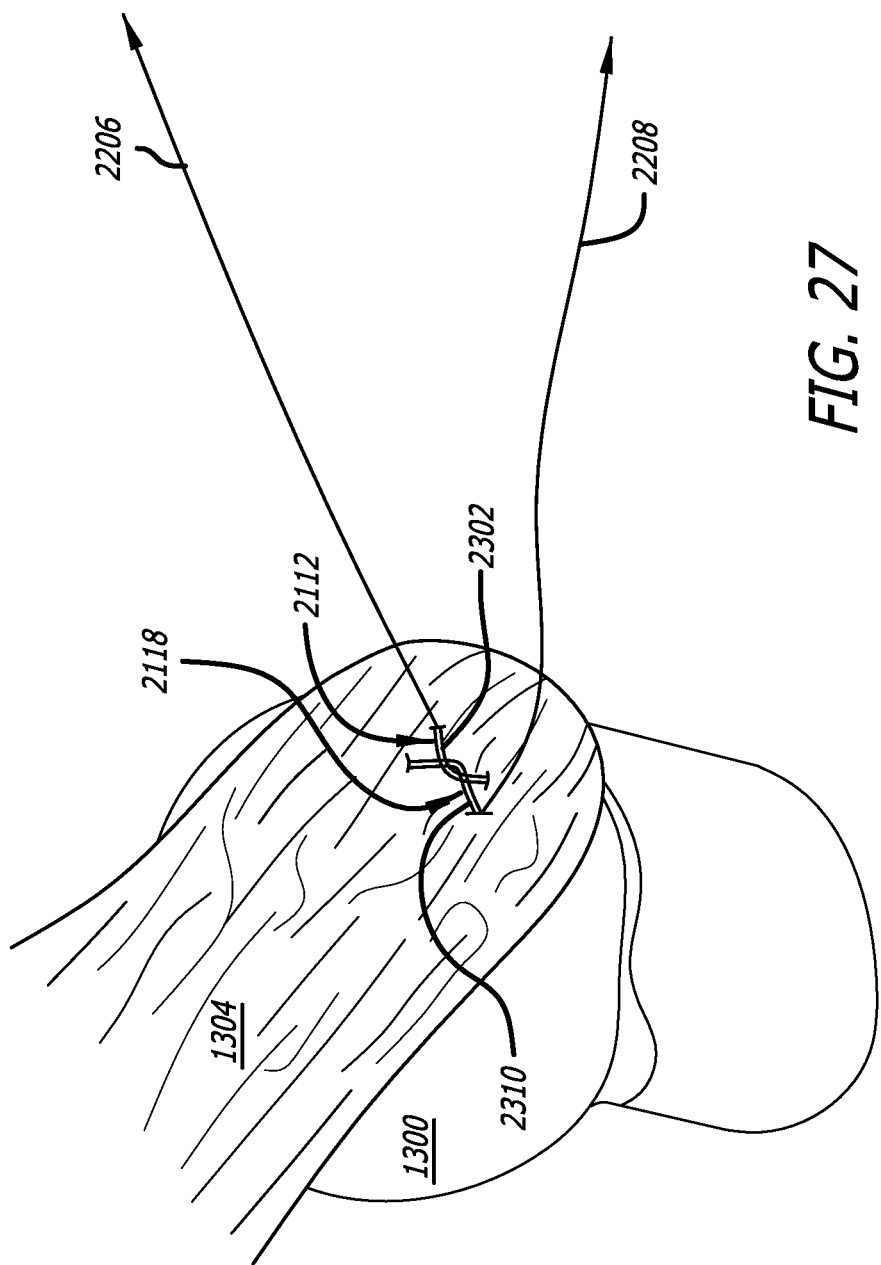
FIG. 27 shows a perspective view of the upper head of the humerus after removal of the guide tool in a double-row repair, in accordance with at least some embodiments.

FIG. 27 shows a perspective view of the upper head of the humerus after removal of the guide tool, in accordance with at least some embodiments. In particular, visible in FIG. 26 is the tissue 1304 over the upper head of the 1300 of the humerus 1302. The guide tool 100 (FIG. 1) has been removed after installation of the four bone anchors. What remains are the suture line 2112 in the form of loop 2302 (though the end of the loop 2302 is not visible, so the loop 2302 appears as two lines) and tightening line 2206. Further visible is the suture line 2118 in the form of loop 2310 (though the end of the loop 2310 is not visible, so the loop 2310 appears as two lines) and tightening line 2208. To finalize the double-row repair, the surgeon pulls on the tightening lines 2206 and 2208, which causes the slipknots (not visible) to slip and thus reduces the size of the loops 2302 and 2310. The loops 2302 and 2310 are thus pulled tight across tissue 1304, holding the tissue 1304 in place, and promoting reattachment in some cases. As shown, in the example case the first and second suture lines cross each other such that, when tightened, the suture lines form an "X" pattern. Other arrangements are possible. Further still, in the example embodiment of FIG. 27 the sutures reside fully over the tissue. However, in other embodiments one or two of the bone anchors may be placed into the bone but not through the tissue, and in those cases the suture created may span the distal end of the tissue.

Figure 28:
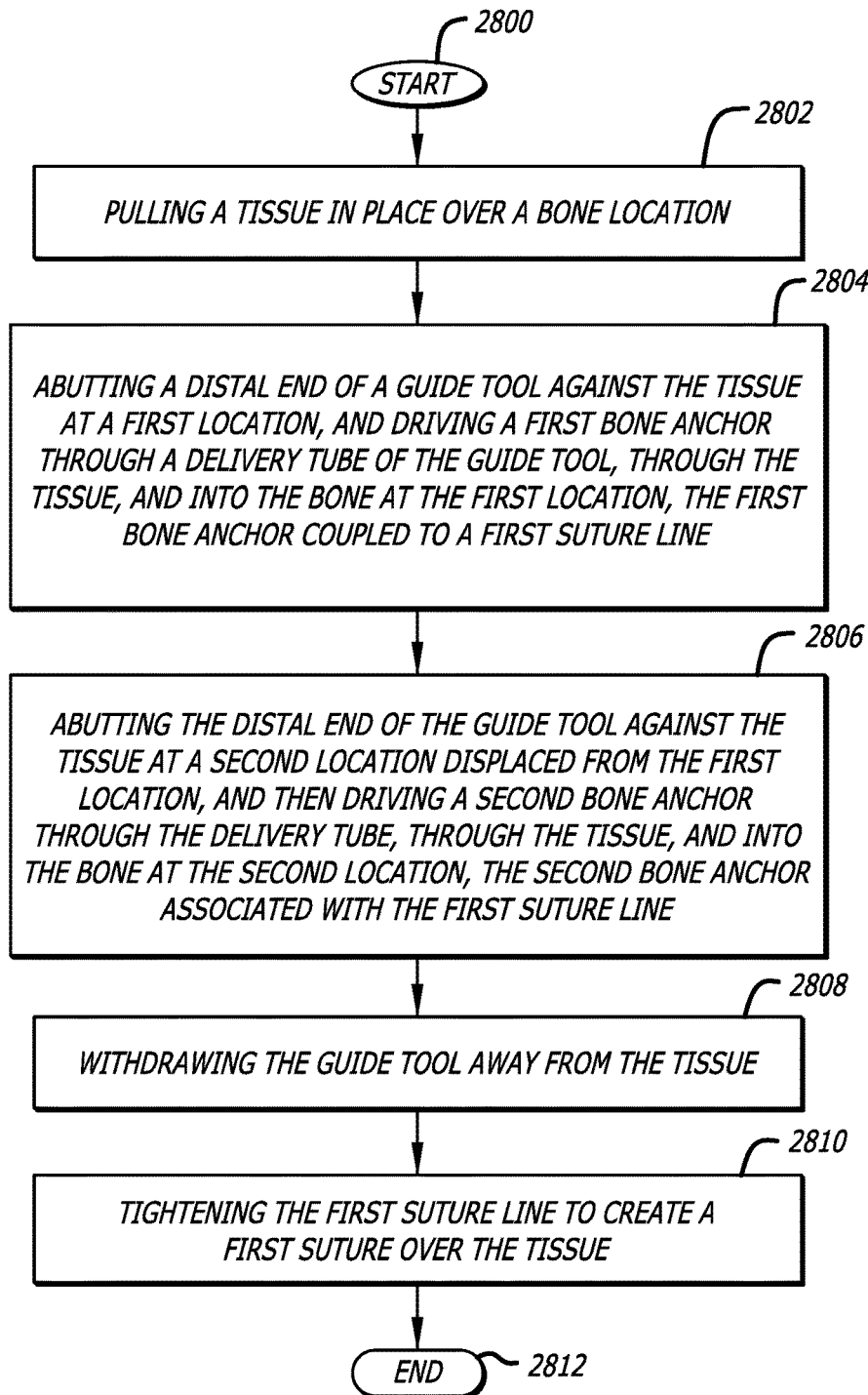
FIG. 28 shows a method in accordance with at least some embodiments.

FIG. 28 shows a method in accordance with at least some embodiments. In particular, the method starts (block 2800) and comprises: pulling a tissue in place over a bone location (block 2802); abutting a distal end of a guide tool against the tissue at a first location, and driving a first bone anchor through a delivery tube of the guide tool, through the tissue, and into the bone at the first location, the first bone anchor coupled to a first suture line (block 2804); abutting the distal end of the guide tool against the tissue at a second location displaced from the first location, and then driving a second bone anchor through the delivery tube, through the tissue, and into the bone at the second location, the second bone anchor associated with the first suture line (block 2806); withdrawing the guide tool away from the tissue (block 2808); and tightening the first suture line to create a first suture over the tissue (block 2810). Thereafter, the method ends (block 2812).

The above discussion is meant to be illustrative of the principles and various embodiments of the present invention. Numerous variations and modifications will become apparent to those skilled in the art once the above disclosure is fully appreciated. For example, the dimensions of the various anchor cartridges have not been expressly discussed, as those dimension depend on the size of the guide tool and the size of the bone anchor. However, the anchor cartridges in some cases are sterilized by inducing a sterilizing gas flow through the device, and thus the open ends of the suture volume are selected not only for loading and deployment of the bone anchors and sutures, but also to enable the gas flow for sterilization purposes. It is intended that the following claims be interpreted to embrace all such variations and modifications.

What is claimed is:

1. A method of connecting tissue to a bone, comprising:
pulling a tissue in place over a bone location;
abutting a distal end of a guide tool against the tissue at a first location;
telescoping a first tack wire through a guide tube of the guide tool;
drilling a distal end of the first tack wire through the tissue and into the bone; and then
bending a proximal end of the first tack wire into a slot within a handle of the guide tool;
driving a first bone anchor through a delivery tube of the guide tool, through the tissue, and into the bone at the first location, the first bone anchor coupled to a first suture line; and then
abutting the distal end of the guide tool against the tissue at a second location displaced from the first location, and then driving a second bone anchor through the delivery tube, through the tissue, and into the bone at the second location, the second bone anchor associated with the first suture line;
withdrawing the guide tool away from the tissue; and
tightening the first suture line to create a first suture over the tissue.

2. The method of claim 1 wherein driving the first bone anchor further comprises:
telescoping a first drill wire though the delivery tube of the guide tool, the delivery tube parallel to the guide tube;
drilling with the first drill wire through the tissue and into the bone to create a first pilot hole in the bone;
removing the first drill wire from the guide tool; and
telescoping the first bone anchor through the delivery tube into the first pilot hole.

3. The method of claim 2:
wherein telescoping the first drill wire further comprises telescoping the first drill wire through a drill guide cartridge mated with a handle of the guide tool, the drill guide cartridge defines a passageway with a longitudinal central axis that is coaxial with a longitudinal central axis of the delivery tube; and
wherein drilling with the first drill wire further comprises drilling with the first drill wire telescoped through the drill guide cartridge.

4. The method of claim 2 wherein telescoping the first bone anchor through the delivery tube further comprises:
mating an anchor cartridge with a handle of the guide tool, the anchor cartridge having a first delivery lumen with the first bone anchor disposed therein, and a second delivery lumen with the second bone anchor disposed therein, and after mating the first delivery lumen is coaxial with the first delivery lumen;
pushing the first bone anchor out the first delivery lumen, through the delivery tube, and into the first pilot hole by way of a delivery camp.

5. The method of claim 4 wherein driving the second bone anchor further comprises:
removing the anchor cartridge from the handle of the guide tool; and then
mating the anchor cartridge with the handle of the guide tool such that the second delivery lumen is coaxial with the delivery tube; and
pushing the second bone anchor out of the second delivery lumen, through the delivery tube, and into a second pilot hole.

6. The method of claim 5 further comprising:
abutting the distal end of the guide tool against the tissue at a third location;

telescoping a third drill wire though the second delivery lumen;

drilling with the third drill wire through the tissue and into the bone to create a third pilot hole in the bone;

removing the third drill wire from the second delivery lumen;

removing the anchor cartridge from the handle of the guide tool;

mating the anchor cartridge with the handle of the guide tool such that a third delivery lumen is coaxial with the delivery tube; and pushing a third bone anchor out of the third delivery lumen, through the delivery tube, and into a third pilot hole.

7. The method of claim 6 further comprising:

abutting the distal end of the guide tool against the tissue at a fourth location;

telescoping a fourth drill wire though the third delivery lumen;

drilling with the fourth drill wire through the tissue and into the bone to create a fourth pilot hole in the bone;

removing the fourth drill wire from the third delivery lumen;

removing the anchor cartridge from the handle of the guide tool;

mating the anchor cartridge with the handle of the guide tool such that a fourth delivery lumen is coaxial with the delivery tube; and pushing a fourth bone anchor out of the fourth delivery lumen, through the delivery tube, and into a third pilot hole.

8. The method of claim 2 wherein, after telescoping the first bone anchor into the first pilot hole, the method further comprises extracting the first suture line from the guide tool through a slot in the delivery tube.

9. The method of claim 2 wherein driving the second bone anchor further comprises:

abutting the distal end of the guide tool against the tissue at the second location displaced from the first location;

telescoping a second tack wire through the guide tube of the guide tool;

drilling a distal end of the second tack wire through the tissue and into the bone; and then bending a proximal end of second tack wire into the slot within the handle of the guide tool;

telescoping a second drill wire though the delivery tube of the guide tool;

drilling with the second drill wire through the tissue and into the bone to create a second pilot hole in the bone;

removing the second drill wire;

telescoping the second bone anchor through the delivery tube into the second pilot hole; and then removing the guide tool including the second tack wire.

10. The method of claim 9:

wherein telescoping the first drill wire further comprises telescoping the first drill wire through a drill guide cartridge mated with a handle of the guide tool, the drill guide cartridge defines a passageway with a longitudinal central axis that is coaxial with a longitudinal central axis of the delivery tube; and wherein drilling with the first drill wire further comprises drilling with the first drill wire telescoped through the drill guide cartridge.

11. The method of claim 10 wherein telescoping the first bone anchor through the delivery tube further comprises:

mating an anchor cartridge with a handle of the guide tool, the anchor cartridge having a first delivery lumen with the first bone anchor disposed therein, and a second delivery lumen with the second bone anchor disposed therein, and after mating the delivery tube is coaxial with the first delivery lumen; and pushing the first bone anchor out the first delivery lumen, through the delivery tube, and into the first pilot hole by way of a delivery camp.

12. The method of claim 11:

wherein telescoping second drill wire further comprises telescoping the second drill wire through the first delivery lumen of the anchor cartridge; and wherein drilling with the second drill wire further comprises drilling with the second drill wire telescoped through first delivery lumen of the anchor cartridge.

13. The method of claim 12 wherein telescoping the second bone anchor through the delivery tube into the second pilot hole further comprises:

removing the anchor cartridge from the handle of the guide tool; and then mating the anchor cartridge with the handle of the guide tool such that the second delivery lumen is coaxial with the delivery tube; and pushing the second bone anchor out of the second delivery lumen, through the delivery tube, and into a second pilot hole.

14. The method of claim 9 wherein the first drill wire and the second drill wires are the same wires.

15. The method of claim 1 wherein tightening the first suture line to create the first suture further comprises tightening a second suture line coupled the second bone anchor, the second suture line having a loop that extends through a loop of the first suture line.

16. The method of claim 1 wherein tightening the first suture line to create the first suture further comprises pulling a tightening end of the first suture line to make a loop defined by the first suture line smaller, the loop of the first suture line extends through an eyelet of an eye splice coupled to the second bone anchor.

17. The method of claim 1 further comprising:

abutting the distal end of the guide tool against the tissue at a third location, and driving a third bone anchor through a delivery tube of the guide tool, through the tissue, and into the bone at the third location, the third bone anchor coupled to a second suture line; and then abutting the distal end of the guide tool against the tissue at a fourth location displaced from the first location, and then driving a fourth bone anchor through the delivery tube, through the tissue, and into the bone at the fourth location, the second bone anchor associated with the second suture line;

tightening the second suture line to create a second suture over the tissue.

* * * * *